United States Patent
Norinobu et al.

(12)

(10) Patent No.: US 6,660,491 B2
(45) Date of Patent: Dec. 9, 2003

(54) PROCESS FOR PRODUCING DIETARY STEROL FATTY ACID ESTERS

(75) Inventors: Seiji Norinobu, Tokyo (JP); Naoko Seo, Hiroshima-ken (JP); Fumi Sato, Hiroshima-ken (JP); Shoji Kaneko, Hiroshima-ken (JP); Mitsumasa Mankura, Hiroshima-ken (JP)

(73) Assignee: Ikeda Food Research Co., Ltd., Hiroshima (JP)

( * ) Notice: Subject to any disclaimer, the term of this patent is extended or adjusted under 35 U.S.C. 154(b) by 5 days.

(21) Appl. No.: 09/988,919

(22) Filed: Nov. 19, 2001

(65) Prior Publication Data

US 2002/0098536 A1 Jul. 25, 2002

(30) Foreign Application Priority Data

Nov. 24, 2000 (JP) ......................... 2000-358092
Feb. 9, 2001 (JP) ......................... 2001-034465
Feb. 9, 2001 (JP) ......................... 2001-034474

(51) Int. Cl.[7] ............................ C12Q 1/44; C12Q 1/46; C12Q 1/60; C12Q 1/00
(52) U.S. Cl. ............................ 435/19; 435/20; 435/11; 435/4; 435/254.22; 426/73
(58) Field of Search ................. 435/19, 20, 11, 435/4, 254.22; 426/73

(56) References Cited

U.S. PATENT DOCUMENTS

| | | | |
|---|---|---|---|
| 3,919,045 A | 11/1975 | Krauch | |
| 5,219,733 A | 6/1993 | Myojo et al. | 435/52 |
| 2002/0098536 A1 * | 7/2002 | Norinobu et al. | 435/52 |

FOREIGN PATENT DOCUMENTS

| | | | |
|---|---|---|---|
| EP | 0 195 311 A | 9/1986 | C11C/3/00 |
| JP | 61-204197 | 9/1986 | |
| JP | 2000-302777 | 10/2000 | |
| WO | WO 99/030569 A | 6/1999 | A23D/7/00 |

OTHER PUBLICATIONS

Shimada, Yuji et al., "Facile purification of tocopherols from soybean oil deodorizer distillate in high yield using lipase," Oct. 2000, Journal of the American Oil Chemists Society, vol. 77, No. 10, pp. 1009–1013: XP002216850.

Wetser Ingmar, "Cholesterol–lowering effect of plant sterols," Jan. 2000, European Journal of Lipid Science and Technology, pp. 37–44: XP002216851.

Eckhardt, J. et al., "Oil processing," Apr. 21, 1997, Internet Article 'Online!,' Retrieved from the Internet: URL:http://www.wsu.edu/gmhyde/433 web pages/433Oil–web–pages/Processing/Process–Edible&Essence Oil.html, retrieve on Oct. 16, 2002: XP002216925.

D.Lombardo et al.; "Esterification of Cholesterol and Lipid–soluble Vitamins by Human Pancreatic Carboxyl Ester Hydrolase" Biochimie, 1980, 62 No. 7; pp. 427–432.

* cited by examiner

Primary Examiner—Louise N. Leary
(74) Attorney, Agent, or Firm—Norris McLaughlin & Marcus

(57) ABSTRACT

A process for enzymatically producing, from a vegetable oil deodorizer distillate, a dietary sterol fatty acid ester superior in flavor qualities (e.g., color, odor and taste) and safety and containing no or little trans fatty acids, wherein the conditions for treatment of the starting material, synthetic reaction and subsequent purification are controlled so that the sterol fatty acid ester becomes applicable as a daily food material, a health food material or a pharmaceutical material. In the process, fatty acid esters, e.g., triacylglycerol, in the vegetable oil deodorizer distillate are previously degraded by hydrolysis with a chemical catalyst, fatty acids produced in the hydrolysis are removed by molecular distillation to give a sterol-containing fraction. The sterol-containing fraction is added with any fat and oil primarily comprising triacylglycerol. The mixture is used as the starting material, and the synthetic reaction is performed under strictly controlled conditions using a lipolytic enzyme. The resulting product undergoes several steps of purification process to provide qualities suitable for a food material.

43 Claims, 2 Drawing Sheets

PRODUCTION PROCESS FOR STEROL FATTY ACID ESTERS

PROCESS FOR PRODUCING DIETARY STEROL FATTY ACID ESTERS

BACKGROUND OF THE INVENTION

1. Field of the Invention

The present invention relates to a process for enzymatically producing a dietary sterol fatty acid ester (i.e., a sterol fatty acid ester for food) from a vegetable oil deodorizer distillate using a lipolytic enzyme.

Particularly, the first aspect of the present invention relates to a process for enzymatically producing a physiologically active, inexpensive dietary sterol fatty acid ester from a vegetable oil deodorizer distillate using a lipolytic enzyme such as a lipase as a catalyst.

The second aspect of the present invention relates to a process for producing a dietary sterol fatty acid ester from a vegetable oil deodorizer distillate at low cost.

The third aspect of the present invention relates to a process for producing a dietary sterol fatty acid ester from a vegetable oil deodorizer distillate at low cost, more specifically a process for producing a dietary sterol fatty acid ester from a vegetable oil deodorizer distillate using a lipolytic enzyme capable of selectively esterifying cis fatty acids.

2. Description of the Related Art

In the purification processes for plant oils such as soybean oil and rapeseed oil, various sterols such as β-sitosterol are usually produced as parts of unsaponifiable matters. Particularly β-sitosterol is known to have an effect of reducing plasma cholesterol level in the body. It has recently become apparent that β-sitostanol, a saturated form of β-sitosterol, has a more potent effect of reducing plasma cholesterol level than β-sitosterol and has been focused.

However, since the above-mentioned free sterols and free stanols are insoluble in the micellar phase in the digestive tract, they are not appropriate for intake to develop their physiological effects. In order to improve the fat-solubility thereof, it has been proposed to modify them in the form of a sterol fatty acid ester. In recent years, it has been attempted to add a sterol fatty acid ester into various food products such as margarine with vegetableterol.

A sterol fatty acid ester has currently been used mostly in a cholesteric liquid crystal and as a hydrophilic base material for pharmaceuticals and cosmetics. Such a sterol fatty acid ester has been produced by chemical synthesis with an acidic or basic catalyst. In chemical synthesis, however, the reaction should be conducted under extreme and severe conditions in most instances, and several problems may arise such as degraded quality of a product and generation of undesirable by-products. Consequently, it is unavoidable to employ highly complicated purification steps after the synthetic reaction. If contemplating the use in food products or pharmaceuticals, there will be a problem that they may be contaminated with by-products or reaction catalysts.

In order to avoid the disadvantages as mentioned above, use of an enzyme in the synthesis reaction has been studied.

Such an enzyme includes a cholesterol esterase and a lipase. Both types of enzymes are categorized as carboxylic acid ester hydrolase. A cholesterol esterase is defined as an enzyme which can break a cholesterol fatty acid ester into a free sterol and a free fatty acid through hydrolysis. A lipase, which usually means triacylglycerol lipase, is defined as an enzyme which can break a glycerol fatty acid ester into glycerol and free fatty acids through hydrolysis.

However, there are found many enzymes having both of cholesterol esterase activity and lipase activity (see D. Lombardo et al., Biochem. Biophys. Acta., 611 (1980), 147-). Literature also indicates that both of a cholesterol esterase and a lipase can catalyze the decomposition reaction of triacylglycerol (see W. E. Momsen et al., Biochem. Biophys. Acta., 486 (1977) 103-). At the present time, considerable numbers of enzymes are known which cannot be clearly specified whether a cholesterol esterase or a lipase.

The above-mentioned enzymes are known to be capable of catalyzing the hydrolysis reaction of a carboxylic acid ester in common cases and, on the other hand, also capable of catalyzing the synthetic reaction of an ester.

Lawrence A. et al. indicated that a sterol ester hydrolase derived from canine pancreatic homogenate, which is known as a cholesterol esterase, can catalyze the synthesis of a cholesterol oleic acid ester from free cholesterol and free oleic acid (Biochem. Biophys. Acta., 231 (1971) 558–560). D. Lombardo et al. also indicated that a cholesterol esterase derived from human pancreatic homogenate can catalyze the synthesis of a cholesterol fatty acid ester (Biochimie et al., 1980, 62, 427–432). Myojo et al. confirmed that a lipase can catalyze the synthesis of a cholesterol fatty acid ester (Japanese Patent Application No. 60-45128).

As mentioned above, it has been shown that cholesterol fatty acid esters can be enzymatically synthesized using enzymes.

However, the conventional production processes for cholesterol fatty acid esters with enzymes as mentioned above have the following problems.

(i) All of the above synthesis examples only make mention of the production of sterol fatty acid esters, and are not intended for the production of sterol fatty acid esters for use as daily food materials, health food materials or pharmaceutical materials. In other words, with respect to the reaction conditions and the subsequent purification process, consideration is not given for achieving good flavor qualities (e.g., color, odor and taste) and safety of the sterol fatty acid esters, which are important factors for daily food materials, health food materials and pharmaceutical materials.

(ii) In the above-mentioned synthesis reactions, a highly purified sterol is used as the starting material for the production of a sterol fatty acid ester. Accordingly, the sterol fatty acid ester produced will inevitably become expensive, which is disadvantage in the application to food products from a cost effectiveness viewpoint.

(iii) A vegetable oil deodorizer distillate produced in the deodorization process for a vegetable oil is rich in unsaponifiable matters (including sterols) and fatty acids. Using the vegetable oil deodorizer distillate as the starting material, a sterol fatty acid ester could be produced at low cost. However, it is known that the vegetable oil deodorizer distillate may also contain undesirable components such as peroxides and trans fatty acids resulting from deterioration of fatty acids. The trans fatty acids are known to be mostly produced in a partial hydrogenation process or a deodorization process under high temperature conditions of a fat and oil. Research indicates that intake of a large amount of trans fatty acids by human increases the risk of developing coronary heart disease. Because of public concern about the trans fatty acid content in various food products particularly in Europe and America, many food products containing reduced amounts of trans fatty acids (e.g., margarine) have recently been developed. Therefore, if a sterol fatty acid ester is synthesized from a vegetable oil deodorizer distillate with an enzymes or chemical catalyst capable of randomly catalyzing the esterification reaction, then the resulting sterol fatty acid ester may contain trans fatty acids or other degraded fatty acids, which is undesirable from a safety viewpoint.

SUMMARY OF THE INVENTION

Accordingly, the object of the first aspect of the present invention is to provide a process for enzymatically producing a physiologically active dietary sterol fatty acid ester from an inexpensive vegetable oil deodorizer distillate using a lipolytic enzyme (e.g., a lipase) at low cost, in which the reaction conditions for synthesis and subsequent purification process of the sterol fatty acid ester are devised so that the resulting sterol fatty acid ester can be superior in flavor properties (e.g., color, odor and taste) and safety and can be used as a daily food material, a health food material or a pharmaceutical material.

The object of the second aspect of the present invention is to provide a process for producing a dietary sterol fatty acid ester suitable for food and containing no or little deteriorated fatty acids including trans fatty acids, at low cost.

The object of the third aspect of the present invention is to provide a process for producing a dietary sterol fatty acid ester suitable for food and containing no or little trans fatty acids at low cost.

DESCRIPTION OF THE PREFERRED EMBODIMENTS

Figure 1:
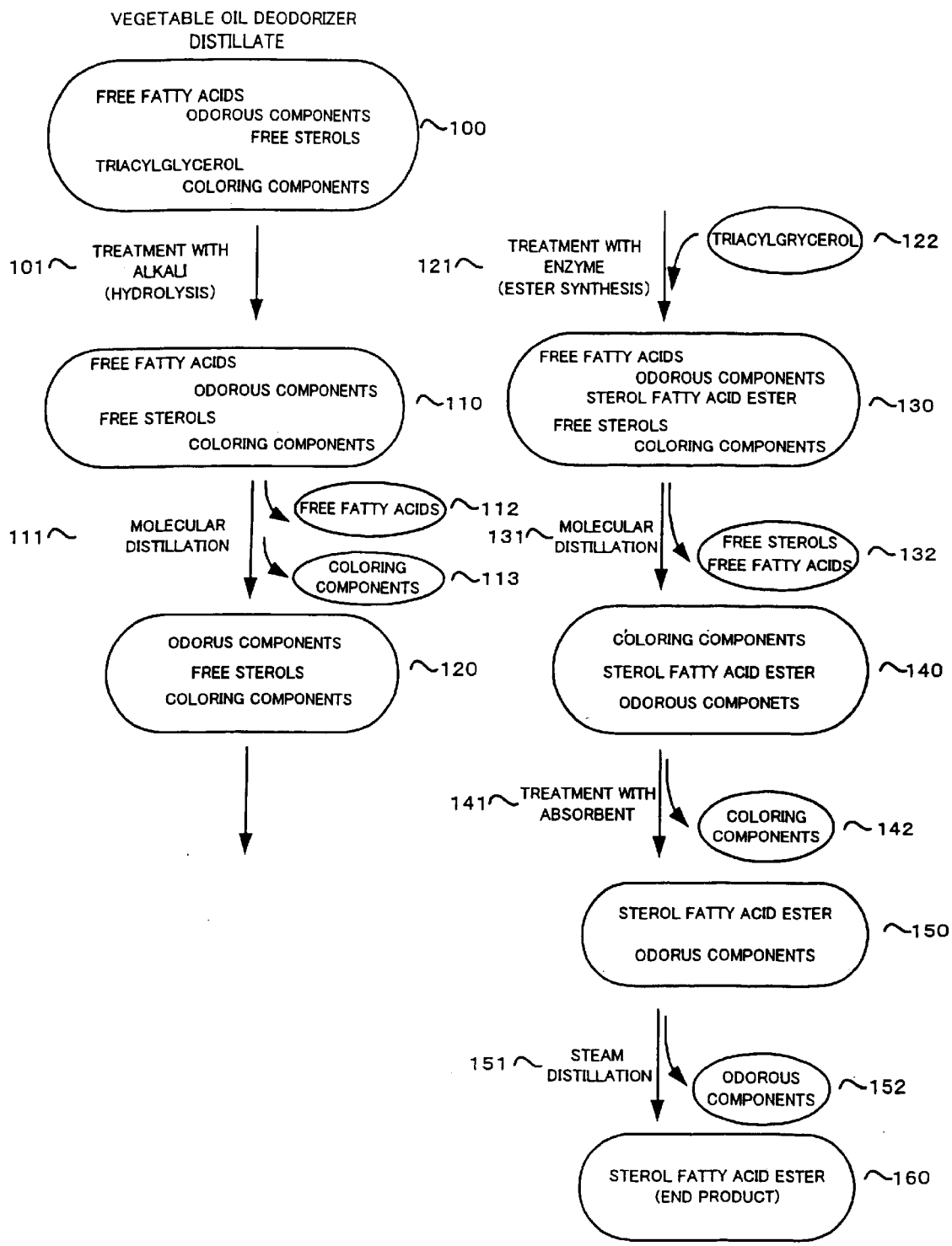
FIG. 1 is a schematic diagram illustrating a process according to the second aspect of the present invention.

Hereinbelow, the three aspects of the present invention will be illustrated.

(a) The feature of the first aspect of the present invention (hereinbelow, also referred to as "first invention" for convenience) resides in a enzymatic production of a physiologically active, inexpensive, plant dietary sterol fatty acid ester from a vegetable oil deodorizer distillate using a lipase as a catalyst (herein, the term "lipolytic enzyme" means an enzyme capable of hydrolyzing a lipid).

According to the process of the first aspect, a vegetable oil deodorizer distillate which is produced as a fraction containing volatile components in the deodorization step (i.e., a step included in the purification process) of a vegetable oil deodorizer distillate is used as a starting material, and a dietary sterol fatty acid ester having a potential physiological activity is enzymatically produced by performing a synthesis reaction of a sterol fatty acid ester from the vegetable oil deodorizer distillate using a lipase under strictly controlled conditions and then subjecting the resulting product to several steps of purification process to provide qualities suitable for a food material.

Besides a lipase, the lipolytic enzyme includes a cholesterol esterase.

(1) The first aspect of the present invention is a process for enzymatically producing a dietary sterol fatty acid ester using a lipolytic enzyme as a catalyst, the process comprising:

providing a vegetable oil deodorizer distillate as a starting material, and performing a synthetic reaction of a sterol fatty acid ester from the vegetable oil deodorizer distillate using a lipolytic enzyme for a predetermined time period under the conditions where temperature and water content are controlled;

performing inactivation of the enzyme, dehydration and removal of the enzyme protein;

performing molecular distillation to primarily remove unreacted sterols and fatty acids;

treating the resulting product with an adsorbent to primarily remove coloring components; and then performing steam distillation to primarily remove odorous components, the sterol fatty acid ester being physiologically active, superior in flavor properties and safety for food.

(2) In the item (1), the vegetable oil deodorizer distillate may be soybean oil deodorizer distillate which is produced in the refining process for soybean oil.

(3) In the item (1), the lipolytic enzyme may be a lipase or cholesterol esterase.

(4) In the item (1), the lipase may be a mesophilic lipase, and the synthetic reaction of a sterol fatty acid ester is performed at 30 to 50° C. within 48 hours.

(5) In the item (1), the lipase may be a thermostable lipase, and the synthetic reaction of a sterol fatty acid ester may be performed at 50 to 80° C. within 24 hours.

(6) In the item (1), the synthetic reaction of a sterol fatty acid ester may be performed using a lipase in the presence of water in an amount of 0.1 wt % or more based on the weight of the starting material.

(7) In the item (1), the molecular distillation may be performed using a molecular distillation apparatus at 133 Pa or lower and 100 to 300° C.

(8) In the item (1), the treatment with an adsorbent may be performed using, as the adsorbent, activated clay, silica gel, activated carbon or a mixture of two or more of them in an amount of 0.1 to 50 wt % based on the weight of the materials to be treated in the presence of a non-polar solvent.

(9) In the item (1), the steam distillation may be performed at 13.3 kPa or lower and 50 to 250° C.

(10) In the item (1), the end product sterol fatty acid ester may have a sterol fatty acid ester content of 90 wt % or more, a peroxide value of 15 or lower, an acid value of 3 or lower and a Gardner color scale of 8 or lower and may be almost odorless as determined by a sensory test.

(11) The sterol fatty acid ester produced by a process as recited in item (1) may be used for food in the form where the sterol fatty acid ester is previously mixed with a fat and oil primarily comprising triacylglycerol.

In the first invention, the vegetable oil deodorizer distillate used as a starting material is any vegetable oil deodorizer distillate which is derived from any plant oil as long as it is produced in the deodorization process for a vegetable oil. Examples of the vegetable oil deodorizer distillate include those of soybean oil, rapeseed oil, palm oil, sunflower seed oil, rice bran oil, corn oil, safflower oil. The vegetable oil deodorizer distillate contains free sterols and free fatty acids, as well as triacylglycerols, diacylglycerols, monoacylglycerols, tocopherols, carotenes, waxes and so on. The free sterols include, for example, β-sitosterol, campesterol, brassicasterol, stigmasterol and choresterol. The free fatty acids and fatty acids contained in triacylglycerols, diacylglycerols and monoacylglycerols include, for example, linoleic acid, oleic acid, palmitic acid, stearic acid, α-linolenic acid and myristic acid.

The vegetable oil deodorizer distillate may be used in the untreated form. However, since it usually contains coloring components and other solid materials, it is preferably used after the removal of unnecessary components such solid materials for example by treatment with an adsorbent or filtration. If cost permits, it may be preferred to previously concentrate the free sterols and fatty acids in the vegetable oil deodorizer distillate for example by distillation or fractionation. Alternatively, additional free sterols and free fatty acids may be added to the vegetable oil deodorizer distillate for use as the starting material. The advantage of the first invention is that both sterols and fatty acids, i.e., base components for the synthesis of a sterol fatty acid ester, already exist in the starting material, i.e., the vegetable oil deodorizer distillate. Use of such a vegetable oil deodorizer distillate as the starting material makes it possible to produce a sterol fatty acid ester at low cost.

In the first invention, the lipase to be used as a catalyst for the hydrolysis or synthetic reaction of the sterol fatty acid ester may be any of those lipolytic enzymes originated from various microorganisms, animals and vegetable. The lipase originated from a microorganism includes, for example, those lipolytic enzymes from microorganisms of the genera Candida, Alcaligenes, Mucor, Rhizopus, Pseudomonas and Geotricum. The lipase originated from an animal includes, for example, those originated from canine pancreatic homogenate. The lipase is preferably one originated from *Candida cylindracea*. When the synthetic reaction is performed under high temperature conditions, a thermostable lipase may be used.

The enzyme may be used in the purified or partially purified form. In the case where a lipase originated from a microorganism, microorganism cell bodies or a culture of the microorganism may also be used. The enzyme may also be in the free state or be immobilized onto any of various supports such as cerite.

The enzymes used in the first invention may also be any one which can catalyze the same reactions as those catalyzed by a lipase. For example, a cholesterol esterase is known to be able to catalyze the same reactions as those catalyzed by a lipase, and therefore can also be used in the first invention.

The conditions to be employed for the synthetic reaction of the sterol fatty acid ester with a lipase should be controlled strictly so that a sterol fatty acid ester having qualities suitable for a food material such as flavor properties (e.g., color, odor and taste) and safety can be produced at low cost.

The amount of the enzyme used may be 50,000 units (U) or less, preferably 10,000 units (U) or less, per gram of the sterols. (1 U is defined as an amount of the enzyme capable of releasing 1 $\mu$mole of a fatty acid from olive oil per minute.) To avoid the deterioration of the enzyme caused by the treatment under heating in the production process and to produce an inexpensive end product, it is desirable to use the enzyme in the smallest possible amount, preferably in an amount of 1,000 units or less per gram of sterols. The enzyme may also be added in a step-wise manner during the synthetic reaction to reduce the amount of the enzyme.

In the first invention, the synthetic reaction of the sterol fatty acid ester proceeds regardless of the presence or absence of water. However, in the absence of water, triacylglycerols contained in the vegetable oil deodorizer distillate may still remain in the product, which is hardly removed in the purification process. Therefore, it is preferred to perform the enzymatic reaction in the presence of 0.1 wt % or more of water. In this case, triacylglycerols, diacylglycerols, monoacylglycerols and so on undergo hydrolysis into free fatty acids and glycerin. The efficiency of the synthetic reaction is more enhanced, the more water is added. However, the water added must be removed in the purification process after the synthesis of the sterol fatty acid ester. Therefore, the amount of water should be minimized for reduction in production cost, and is preferably 100% or less based on the weight of the vegetable oil deodorizer distillate, i.e., the starting material.

To minimize the thermal degradation of the product during the synthetic reaction, the reaction is preferably performed at a lower temperature for a shorter time period. For example, when a mesophilic lipase is used, the synthesis is performed at 30 to 50° C. within 48 hours. When the synthesis is performed at a lower temperature, a lipase which can readily exert its enzymatic activity at such a lower temperature may be used.

Because of their very high melting points, sterols (one base material) tend to have poor compatibility with fatty acids, i.e., the other base material. Therefore, in some cases, the efficiency of the synthetic reaction of the sterol fatty acid ester with the enzyme may become low. To overcome this problem, the synthetic reaction is performed at a higher temperature, preferably at 50 to 80° C. within 24 hours using a thermostable lipase. In this case, however, thermal deterioration of the sterol fatty acid ester may proceed more aggressively or the lipase may be inactivated during the reaction. Therefore, a substance having anti-oxidant effect, e.g., Vitamin E and tea polyphenol, may be added to prevent the thermal or oxidative deterioration of the sterol fatty acid ester, and a substance capable of inhibiting the inactivation of an enzyme, e.g., a salt such as bile salt, a carbohydrate and a protein, may be added to prevent the inactivation of the enzyme.

To enhance the efficiency of the synthetic reaction, the reaction is usually performed while stirring the reaction materials, but optionally may be performed in a static state. When the reaction is performed in a static state, an emulsifying agent or the like may be added. An organic solvent such as hexane may also be used to enhance the efficiency of the reaction. In this case, however, the solvent must be removed, which may increase the production cost.

The purification of the sterol fatty acid ester will be illustrated hereinbelow.

In the first invention, in order to achieve the production of a sterol fatty acid ester having qualities suitable for a food material (e.g., color, odor and taste) and superior in safety at low cost, the purification process after the synthetic reaction must be performed carefully.

At first, after the synthetic reaction of the sterol fatty acid ester is completed, inactivation of the enzyme, dehydration and removal of the enzyme protein are performed. The inactivation of the enzyme is achieved by stirring the reactants for 30 min. or longer at 60° C. or higher for a mesophilic lipase or 80° C. or higher for a thermostatic lipase. The dehydration is performed by treating the reactant at 80° C. or higher for a predetermined time period under a reduced pressure of 13.3 kPa or lower. The removal of the enzyme protein can be achieved by filtration using a conventional filter paper, filter cloth or any other type of filtration means. If the removal of the enzyme protein is insufficient, then deterioration in quality such as coloration of the sterol fatty acid ester may be caused by the heating in subsequent processes. Therefore, the enzyme protein must be removed completely. For more effective removal, it is preferred to previously add a filter aid, e.g., diatom earth, and then stirred and filtered.

Next, molecular distillation is performed to remove the unreacted sterols, fatty acids and other impurities such as tocopherols. The sterol fatty acid ester, i.e., reaction product, given after the removal of the enzyme protein contains various impurities including unreacted sterols and fatty acids, tocopherols, coloring components and odorous components, and these impurities must be removed.

At first, molecular distillation is performed to remove sterols, fatty acids, tocopherols efficiently. The sterol fatty acid ester is given as a residue, while unreacted sterols and fatty acids, tocopherols and parts of coloring components and odorous components are given as a distillate. The apparatus for the molecular distillation may be of falling film type or centrifugal type. The molecular distillation is preferably performed at 133 Pa or lower and 100 to 300° C., more preferably at 13.3 Pa or lower and 150 to 250° C. The molecular distillation may be performed repeatedly for several times.

Subsequently, treatment with an adsorbent is performed to remove coloring components. The sterol fatty acid ester (residue) after the molecular distillation contains coloring components derived from the starting material and coloring components resulting from the heating during the distillation, as well as odorous components. In the first invention, to remove the coloring components efficiently, the sterol fatty acid ester is treated with an adsorbent. The adsorbent includes those conventionally used for purification of fats and oils, such as activated clay, acidic clay, activated carbon, silica, silica-magnesia and so on, and is preferably activated clay, activated carbon or silica. These may be used singly or in combination. The adsorbent is preferably added in an amount of 0.1 to 50 wt %, more preferably 1 to 20 wt %, based on the weight of the material to be treated. For more efficient decoloration, it is preferred to perform the treatment with the adsorbent in a non-polar solvent such as hexane. The solvent is preferably used in 0.1 to 50 volumes, more preferably 0.5 to 20 volumes, of the material to be treated. When a non-polar solvent is not used, the decoloration is performed by adding the adsorbent to the material to be treated and then stirring at 40 to 150° C. for a predetermined time period. This procedure may be performed under normal atmospheric pressure. However, to prevent the deterioration of the material to be treated and decolor it more effectively, the procedure is preferably performed under reduced pressure. A lower pressure is preferred, such as 13.3 kPa or lower.

After the treatment, the adsorbent is removed by filtration using any conventional filtrating means, such as a filter paper, a filter cloth or any other filtration means. For more effective removal, it is preferred to previously add a filter aid, e.g., diatom earth, and then stirred and filtered. In the case where a non-polar solvent is used, it is preferred to dissolve the material to be treated in the non-polar solvent previously, and then add the adsorbent thereto and stir the resulting reaction mixture at 0 to 60° C. for a predetermined time period. The adsorbent is removed in the same manner as stated above, and then the non-polar solvent is removed by distillation. When the removal of the coloring components to a higher degree is required or the material to be decolored has a darker color, it is preferred to repeat the treatment with the adsorbent for several times. In this case, additional any adsorbent may be added after the filtration of the preceding adsorbent and then another round of procedure is performed in the same manner. When a non-polar solvent is used, additional any adsorbent may be added after the proceeding round of addition of an adsorbent, stirring and filtration without the need of removal of the solvent, and then the subsequent round is performed. The solvent is removed after filtration in the final round is completed. Alternatively, the material given after the molecular distillation may be treated with an acid or alkali prior to the treatment with the adsorbent, thereby achieving the decoloration more effectively. In this case, the material to be treated may be dissolved in a non-polar solvent (e.g., hexane) to make the material in a micellar state, and then treated with an acid or alkali.

As the final step, steam distillation is performed to remove odorous components and so on. For use as a food material, the sterol fatty acid ester after the decoloration is required to remove odorous components derived from the starting material or generated in the proceeding steps. When the decoloration is performed using an organic solvent, the organic solvent may remain in the product even after the removal of the solvent. Therefore, the remaining organic solvent must be removed completely. Steam distillation makes it possible to remove the odorous components and the remaining organic solvent in the product. In the steam distillation, any type of apparatus may be used, including those of continuous type, semi-continuous type and batch type. The steam distillation is desirable to perform under the conditions of 13.3 kPa or lower and 50 to 250° C., preferably 1330 Pa or lower and 100 to 200° C. The steam distillation may be repeated for several times.

The sterol fatty acid ester thus produced can be used as a food material as-is. However, because of poor fluidity and workability, the sterol fatty acid ester is preferably used in the form where it is mixed with other fat and oil, such as those primarily comprising triacylglycerol. In this case, any mixing ratio may be employed depending on the intended use. Preferably, the fat and oil may be mixed in an amount of 30 to 300 wt % based on the weight of the sterol fatty acid ester. The fat and oil primarily comprising triacylglycerols may be a dietary fat and oil, such as soybean oil, rapeseed oil. Other fat and oil may also be mixed, including those containing other component such as diacylglycerols. In the first invention, it is possible to leave triacylglycerols, diacylglycerols or monoacylglycerols contained in the vegetable oil deodorizer distillate, i.e., the starting material, to remain in the product by controlling the water content during the reaction with the enzyme. As a result, a sterol fatty acid ester having improved fluidity can be produced.

The sterol fatty acid ester, the end product of the first invention, is almost tasteless, odorless and pale yellow in color and has superior safety, and therefore is suitable a daily food material, a health food material and a pharmaceutical material. The sterol fatty acid ester has the potential effect of reducing cholesterol level. Accordingly, the sterol fatty acid ester is expected to be used, as a functional material, in a daily food product, e.g., margarine and dressing, and a health food product, and is also expected to be used in a pharmaceutical in the future.

(b) The second aspect of the present invention will be explained hereinbelow.

The feature of the second aspect of the present invention (hereinbelow, also referred to as "second invention" for convenience) resides in a production of a highly safe, inexpensive dietary sterol fatty acid ester containing no or little deteriorated fatty acids, from a vegetable oil deodorizer distillate.

The second aspect is schematically described with reference to FIG. 1. A vegetable oil deodorizer distillate is used as a starting material which is produced, as a fraction containing volatile materials, in the deodorization process (a step included in the purification process) for a vegetable oil (Step 100). Fatty acid esters, e.g., triacylglycerols, in the vegetable oil deodorizer distillate are previously degraded (Step 110) by hydrolysis with a chemical catalyst (Step 101). The resulting fatty acids (Steps 112 and 113) are removed by molecular distillation (Step 111) to give a sterol-containing fraction (Step 120).

Subsequently, the sterol-containing fraction is added with a fat and oil primarily comprising triacylglycerols and the resulting mixture is provided as the starting material (Step 122). The mixture is subjected to a synthetic reaction of a sterol fatty acid ester (Step 130) with a lipolytic enzyme as a catalyst under the strictly controlled conditions (Step 121). For providing qualities suitable for a food material, the resulting product is subjected to several steps of purification (Steps 131, 141 and 151), whereby a highly safe, inexpensive dietary sterol fatty acid ester containing no or little deteriorated fatty acids including trans fatty acids (Step 160) can be produced enzymatically.

(1) Accordingly, the second aspect of the present invention is a process for producing a dietary sterol fatty acid ester comprising adding a lipolytic enzyme to a mixture of a sterol-containing fraction and a fat and oil primarily comprising triacylglycerols to produce a sterol fatty acid ester and then purifying the sterol fatty acid ester through a predetermined purification process, the process comprising:

providing, as a source of sterols, a vegetable oil deodorizer distillate which is produced in the deodorization process of a vegetable oil;

performing hydrolysis of fatty acid esters in the vegetable oil deodorizer distillate;

performing a first molecular distillation to primarily remove fatty acids to collect a sterol-containing fraction;

performing a synthetic reaction of a sterol fatty acid ester using a mixture of the sterol-containing fraction and a fat and oil primarily comprising triacylglycerols as a starting material, with a lipolytic enzyme for a predetermined time period under the conditions where temperature and water content are controlled;

as a first purification step, performing a second molecular distillation to primarily remove unreacted sterols and fatty acids;

as a second purification step, treating the resulting product with an adsorbent to primarily remove coloring components; and then as a third purification step, performing steam distillation to primarily remove odorous components, while controlling the temperature for the purification to prevent the production of trans fatty acids, the sterol fatty acid ester being superior in physical properties, flavor properties and safety for food.

(2) In the item (1), the hydrolysis may be performed for the purpose of converting trans fatty acids and deteriorated fatty acids such as oxidized fatty acids in the vegetable oil deodorizer distillate into their free states for easy removal of the fatty acids from the reaction product.

(3) In the item (1), soybean oil deodorizer distillate which is produced in the refining process of soybean oil may be used as the sauce of sterols.

(4) In the item (1), the hydrolysis may be performed using an acidic or alkaline catalyst.

(5) In the item (1), the first molecular distillation may be performed at 13.3 Pa or lower and 100 to 200° C.

(6) In the item (1), in the first molecular distillation, the reaction mixture may be distilled at 13.3 Pa or lower and 100 to 200° C. to collect a sterol-containing fraction as a residue and the sterol-containing fraction may be then distilled at 13.3 Pa or lower and 170 to 250° C. to collect a sterol-containing fraction as a distillate.

(7) In the item (1), wherein the synthetic reaction of a sterol fatty acid ester may be performed using a lipolytic enzyme having an activity of hydrolyzing a sterol fatty acid ester as the lipolytic enzyme.

(8) In the item (1), the synthetic reaction of a sterol fatty acid ester may be performed using an enzyme capable of hydrolyzing a sterol fatty acid ester which is originated from a microorganism of the genus Pseudomonas as the lipolytic enzyme.

(9) In the item (7) or (8), the lipolytic enzyme may be a cholesterol esterase.

(10) In the item (1), the synthetic reaction of a sterol fatty acid ester may be performed using an enzyme having an activity of hydrolyzing triacylglycerol as the lipolytic enzyme.

(11) In the item (1), the synthetic reaction of a sterol fatty acid ester may be performed using an enzyme capable of hydrolyzing triacylglycerol which is originated from a microorganism of the genus Candida as the lipolytic enzyme.

(12) In the item (10) or (11), the lipolytic enzyme may be a lipase.

(13) In the item (1), the synthetic reaction of a sterol fatty acid ester may be performed at 30 to 60° C. within 48 hours in the presence of water of 0.1 to 50 wt % based on the weight of the fat and oil primarily comprising triacylglycerol.

(14) In the item (1), the second molecular distillation as the first purification step may be performed at 13.3 Pa or lower and 100 to 250° C.

(15) In the item (1), the treatment with an adsorbent as the second purification step is performed at 100° C. or lower using, as the adsorbent, activated clay, silica gel, activated carbon or a mixture of two or more of them in an amount of 0.1 to 50 wt % based on the weight of the material to be treated.

(16) In the item (1), the steam distillation as the third purification step may be performed at 13.3 kPa or lower and 50 to 150° C.

(17) In the item (1), the end product sterol fatty acid ester may have a sterol fatty acid ester content of 90 wt % or more, a trans fatty acid content in the constitutive fatty acids of 2 wt % or lower, a peroxide value of 10 or lower, an acid value of 1 or lower and a Gardner color scale of 6 or lower and may be almost odorless as determined by a sensory test.

(18) In the item (1), soybean oil may be used as the fat and oil primarily comprising triacylglycerols to be added to the sterol-containing fraction, and the end product sterol fatty acid ester may have a melting point of 20 to 40° C. and a trans fatty acid content in the constitutive fatty acids of 2 wt % or lower.

(19) In the item (1), rapeseed oil may be used as the fat and oil primarily comprising triacylglycerols to be added to the sterol-containing fraction, and the end product sterol fatty acid ester may have a melting point of 20 to 40° C. and a trans fatty acid content in the constitutive fatty acids of 2 wt % or lower.

(20) In the item (1), olive oil may be used as the fat and oil primarily comprising triacylglycerols to be added to the sterol-containing fraction, and the end product sterol fatty acid ester may have a melting point of 25 to 45° C. and a trans fatty acid content in the constitutive fatty acids of 1 wt % or lower.

(21) In the item (1), palm oil may be used as the fat and oil primarily comprising triacylglycerols to be added to the sterol-containing fraction, and the end product sterol fatty acid ester may have a melting point of 40 to 100° C. and a trans fatty acid content in the constitutive fatty acids of 1 wt % or lower.

(22) In the item (1), palm oil may be used as the fat and oil primarily comprising triacylglycerol to be added to the sterol-containing fraction, a thermostable lipolytic enzyme may be used, and the end product sterol fatty acid ester may have a melting point of 40 to 100° C. and a trans fatty acid content in the constitutive fatty acids of 1 wt % or lower.

(23) In the item (1), a fish oil may be used as the fat and oil primarily comprising triacylglycerol to be added to the sterol-containing fraction, and the end product sterol fatty acid ester may have a melting point of −10 to 20° C. and a trans fatty acid content in the constitutive fatty acids of 2 wt % or lower.

The second aspect of the present invention is described in detail hereinbelow with reference to FIG. 1.

First, a process for degradation of a vegetable oil deodorizer distillate in Step 100 is illustrated.

In the second invention, the vegetable oil deodorizer distillate used as a starting material is any vegetable oil deodorizer distillate which is derived from any vegetable oil as long as it is produced in the deodorization process for a vegetable oil. Examples of the vegetable oil deodorizer distillate include those of soybean oil, rapeseed oil, palm oil, sunflower seed oil, rice bran oil, corn oil, safflower oil. The vegetable oil deodorizer distillate contains free sterols and free fatty acids, as well as triacylglycerols, diacylglycerols, monoacylglycerols, tocopherols, carotenes, waxes and so on.

The free sterols include, for example, β-sitosterol, campesterol, brassicasterol, stigmasterol and choresterol. The free fatty acids and fatty acids contained in triacylglycerols, diacylglycerols and monoacylglycerols include, for example, linoleic acid, oleic acid, palmitic acid, stearic acid, α-linolenic acid and myristic acid. Particularly in linolenic acid which contains relatively many unsaturated bonds, a trans-type one constitutes a high proportion. Therefore, soybean oil deodorizer distillate which is rich in linolenic acid may have a high trans fatty acid content.

The vegetable oil deodorizer distillate usually contains coloring components or other solid materials. Therefore, when it is used as-is for synthesis of a sterol fatty acid ester, some difficulty may occur in the purification of the sterol fatty acid ester such as decoloration and deodorization.

In the second invention, fatty acid esters, e.g., triacylglycerols in the vegetable oil deodorizer distillate are previously hydrolyzed (Step 101) and the resulting fatty acids (Step 110) are then removed by molecular distillation, i.e., first molecular distillation (Step 111) to give a sterol-containing fraction (Step 120). The sterol-containing fraction is used as the starting material for the synthetic reaction of a sterol fatty acid ester.

In this manner, fatty acid esters, e.g., triacylglycerol, are previously converted into free fatty acids (Step 110), whereby deteriorated fatty acids, e.g., trans fatty acids and oxidized fatty acids, can be readily removed by molecular distillation (Step 111).

The catalyst to be used in the hydrolysis of the fatty acid esters, i.e., triacylglycerols, in the vegetable oil deodorizer distillate may be any one as long as it is available for food products, such as a chemical catalyst, e.g., an acid and an alkali. The catalyst includes an acid such as hydrochloric acid, sulfuric acid, acetic acid, citric acid, phosphoric acid, oxalic acid, malic adic and nitric acid; and an alkali such as sodium hydroxide, potassium hydroxide, ammonia, sodium hydrogencarbonate, magnesium hydroxide and calcium hydroxide.

Generally for the hydrolysis of the fatty acid esters, as stated above, a lipolytic enzyme such as a lipase may also be used in place of a chemical catalyst. When a lipolytic enzyme is used in the hydrolysis of the fatty acid esters in the vegetable oil deodorizer distillate, however, a synthesis of a sterol fatty acid ester may proceed concurrently with the degradation of triacylglycerols and so on. For this reason, it is improper to use a lipolytic enzyme, e.g., a lipase, in the hydrolysis of the fatty acid esters.

In the hydrolysis of the fatty acid esters (Step 101), any catalyst concentration, any reaction temperature and any reaction time may be employed. However, it is preferred to perform the reaction at 150° C. or lower within several hours, since an excess reaction may cause undesirable phenomena such as deterioration of every components in the vegetable oil deodorizer distillate and coloration of the resulting product.

After the synthetic reaction is completed, the neutralization is performed with a suitable acid or alkali, followed by washing with water to remove glycerin, salts and so on which may be produced in the synthesis and the chemical catalyst. After washing with water, resulting product is subjected to aqueous/oily phase separation and then heated at about 60 to 120° C. for a predetermined time period under reduced pressure to remove water therefrom (Step 110).

The vegetable oil deodorizer distillate after the removal of water (Step 110) is fractionated by molecular distillation (Step 111). In the second invention, this procedure is made for the purpose of removing trans fatty acids, peroxides of fatty acids and so on which are present as deteriorated fatty acids (Step 112, 113), and is performed at 13.3 Pa or lower and 100 to 200° C. In this manner, the fatty acids can be removed as a distillate and a sterol-containing fraction can be obtained as the residue (Step 120).

The residue (Step 120) given by the molecular distillation (Step 111) may also be additionally treated at 13.3 Pa or lower and 170 to 250° C. to remove coloring components and other solid materials in the vegetable oil deodorizer distillate, thereby giving a sterol-containing fraction (Step 120) as a distillate. This additional treatment makes the subsequent purification process (particularly decoloration and deodorization) more easy and also makes the qualities, e.g., color, odor, taste, of the end product better.

Next, Steps 121, 122 and 130 involved in the synthesis of a sterol fatty acid ester (Step 130) are described below.

The synthesis of a sterol fatty acid ester is performed using two starting materials; the sterol-containing fraction (Step 120) produced by the degradation and distillation of the vegetable oil deodorizer distillate; and any fat and oil primarily comprising triacylglycerols (Step 122).

The fat and oil primarily comprising triacylglycerols includes soybean oil, rapeseed oil, olive oil, palm oil, sunflower seed oil, corn oil, cotton seed oil, sesame oil, rice bran oil, coconut oil, peanut oil, beef fat, hog fat, chicken fat and fish oils. These fats and oils may be used singly or in combination. In the second invention, use of any fat and oil can provide a sterol fatty acid ester having a desired melting point.

In recent years, some fatty acids is known to have physiological activities. In the second invention, a fat and oil rich in a desired fatty acid may be selected to exert the physiological functions of the fatty acid.

The fat and oil may be added in an amount of 50 to 500 wt %, preferably 100 to 300 wt %, based on the weight of the sterol-containing fraction.

The lipolytic enzyme to be used as a catalyst for the synthesis of the sterol fatty acid ester includes a lipase and a cholesterol esterase. The enzyme may be any of those originated from various microorganisms, animals and vegetable. The enzyme originated from a microorganism include, for example, those from microorganisms of the genera Pseudomonas, Alcaligenes, Candida, Mucor, Rhizopus and Geotricum. The enzyme originated from an animal include, for example, those originated from porcine pancreas.

The enzyme used in the second invention may be one capable of hydrolyzing a sterol fatty acid ester, i.e., a cholesterol esterase, or one capable of hydrolyzing triacylglycerol, i.e., a lipase. The former enzyme includes those originated from a microorganism of genus Pseudomonas, and the latter enzyme includes those originated from a microorganism of genera Alcaligenes and Candida. There are known a number of enzymes having both an activity of hydrolyzing a sterol fatty acid ester and an activity of hydrolyzing triacylglycerols. In the second invention, any lipolytic enzyme which is able to catalyze the synthetic reaction of a sterol fatty acid ester can be used without concern for enzyme-classificatory constrains.

When the synthetic reaction is performed under high temperature conditions, a thermostable lipolytic enzyme may be used. The enzyme may be used in the purified or partially purified form. In the case where a lipolytic enzyme originated from a microorganism, microorganism cell bodies or a culture of the microorganism may also be used. The enzyme may also be in the free state or be immobilized onto any of various supports such as cerite.

The conditions to be employed for the synthetic reaction of the sterol fatty acid ester with a lipolytic enzyme should be controlled strictly so that a sterol fatty acid ester having qualities suitable for a food material such as flavor properties, e.g., color, odor and taste, and safety can be produced at low cost. The reaction conditions are described in the following.

As in the case of the first invention, the enzyme may be used in an amount of 50,000 units (U) or less, preferably 10,000 units (U) or less per gram of the sterols. To avoid the deterioration of the enzyme caused by the treatment under heating in the production process and to produce the end product at low cost, it is desirable to use the enzyme in a smallest possible amount, preferably in an amount of 5,000 units or less per gram of sterols in the starting material. The enzyme may also be added in a step-wise manner during the synthetic reaction to reduce the amount of the enzyme.

In the second invention, in the presence of no water or an extremely small amount of water, triacylglycerols or a trace amount of diacylglycerols or monoacylglycerols may still remain in the product, which is hardly removed in the subsequent purification process. Therefore, it is preferred to perform the enzymatic reaction in the presence of 0.1 wt % or more of water. In this case, triacylglycerols and co-existing diacylglycerols, monoacylglycerols and so on undergo hydrolysis into free fatty acids and glycerin. The fatty acids produced by this hydrolysis can also be utilized as the starting material for the synthetic reaction of the sterol fatty acid ester.

The efficiency of the synthetic reaction is more enhanced, the more water is added. However, the water added must be removed in the purification process after the synthesis of the sterol fatty acid ester. Therefore, the amount of water should be minimized for reduction in production cost, and is preferably 300% or less based on the weight of the vegetable oil deodorizer distillate, i.e., the starting material.

To minimize the thermal degradation of the product during the synthetic reaction, the reaction is preferably performed at a lower temperature for a shorter time period, usually at 30 to 60° C. within 48 hours. When the synthesis is performed at a lower temperature, a lipolytic enzyme which can readily exert its enzymatic activity at such a lower temperature may be used.

As in the case of the first invention, because of their very high melting points, sterols (one base material) tend to have poor compatibility with fatty acids (i.e., the other base material). Therefore, in some cases, the efficiency of the synthetic reaction of the sterol fatty acid ester may become low. To overcome this problem, the synthetic reaction is performed at a higher temperature, preferably at 50 to 90° C. within 24 hours using a thermostable lipolytic enzyme. In this case, however, thermal deterioration of the sterol fatty acid ester may proceed more aggressively or the enzyme may be inactivated during the reaction. Therefore, a substance having anti-oxidant effect, e.g., Vitamin E and tea polyphenol, may be added to prevent the thermal or oxidative deterioration of the sterol fatty acid ester, and a substance capable of inhibiting the inactivation of an enzyme, e.g., a salt such as bile salt, a carbohydrate and a protein, may be added to prevent the inactivation of the enzyme.

To enhance the efficiency of the synthetic reaction, the reaction is usually performed while stirring the reaction materials, but optionally may be performed in a static state. When the reaction is performed in a static state, an emulsifying agent or the like may be added. An organic solvent such as hexane may also be used to enhance the efficiency of the reaction. In this case, however, the solvent must be removed, which may increase the production cost.

After the synthetic reaction of the sterol fatty acid ester is completed, inactivation of the enzyme, dehydration and removal of the enzyme protein are performed. The inactivation of the enzyme is achieved by stirring the reactants at 60 to 100° C. for about 30 to 120 min. The dehydration is performed by treating the reactant at 60 to 120° C. for a predetermined time period under reduced pressure. The removal of the enzyme protein can be achieved by filtration using a conventional filter paper, filter cloth or any other type of filtration means. If the removal of the enzyme protein is insufficient, then deterioration in quality such as coloration of the sterol fatty acid ester may be caused by the heating in subsequent processes. Therefore, the enzyme protein must be removed completely. For more effective removal, it is preferred to previously add a filter aid, e.g., diatom earth, and then stirred and filtered. As described above, the sterol fatty acid ester can be synthesized.

Next, the purification process for the sterol fatty acid ester is explained.

In the second invention, in order to produce a sterol fatty acid ester having qualities suitable for a food material, e.g., color, odor and taste, and superior in safety at low cost, the purification of the product given by the synthetic reaction should be performed carefully. Particularly when the purification is performed at high temperatures, generation of trans fatty acids and peroxides may occur. Therefore, the temperature conditions must be controlled strictly.

As a first purification step, a molecular distillation (second molecular distillation) (Step 131) is performed to primarily remove the unreacted sterols and fatty acids (Step 132). The sterol fatty acid ester, i.e., reaction product, given after the removal of the enzyme protein contains various impurities including unreacted sterols and fatty acids and other trace components, and these impurities must be removed.

In the second invention, molecular distillation (Step 131) is first performed to efficiently remove sterols and fatty acids (Step 132). The sterol fatty acid ester is given as a residue (Step 140), while unreacted sterols and fatty acids and parts of odorous components are removed as a distillate (Step 132). The apparatus for the molecular distillation may be of falling film type, centrifugal type or any other type of short pass distillation apparatus. Any apparatus may be used as long as it can achieve the desired vacuum pressure and temperature and can remove the desired free sterols, free fatty acids and other trace components.

The molecular distillation is preferably performed at 133 Pa or lower and 100 to 300° C., more preferably at 13.3 Pa or lower and 100 to 250° C. The molecular distillation may be performed repeatedly for several times. In this step, it is possible to remove odorous components which cannot be removed in the steam distillation (Step 151), i.e., the third step of the purification process. On the other hand, some heating odor may be generated in this step. In this case, additional molecular distillation is required prior to the steam distillation (Step 151) to produce the end product without odorous components efficiently.

Subsequently, as a second purification step (Step 141), coloring components (Step 142) are primarily removed. The sterol fatty acid ester after the molecular distillation (Step 140) contains coloring components derived from the starting material and coloring components resulting from the heating during the distillation, as well as odorous components.

In the second invention, to remove the coloring components (Step 142) efficiently, the sterol fatty acid ester is treated with an adsorbent (Step 141). The adsorbent includes those adsorbent conventionally used for purification of fats and oils, such as activated clay, acidic clay, activated carbon, silica gel, silica-magnesia and so on, and is preferably activated clay, activated carbon or silica gel. These may be used singly or in combination. The adsorbent is preferably added in an amount of 0.1 to 50 wt %, more preferably 1 to 20 wt %, based on the weight of the sterol fatty acid ester to be treated. For more efficient decoloration, it is preferred to perform the treatment with the adsorbent in a non-polar solvent such as hexane. The solvent is preferably used in 0.1 to 50 volumes, more preferably 0.5 to 20 volumes, of the material to be treated. When a non-polar solvent is not used, the decoloration is performed by adding the adsorbent to the material to be treated and then stirring at 40 to 150° C. for a predetermined time period. This procedure may be performed under normal atmospheric pressure. However, to prevent the deterioration of the material to be treated and decolor it more effectively, the procedure is preferably performed under reduced pressure. A lower pressure is preferred, such as 13.3 kPa or lower.

After the treatment, the adsorbent is removed by filtration using any conventional filtrating means, such as a filter paper, a filter cloth or any other filtration means. For more effective removal, it is preferred to previously add a filter aid, e.g., diatom earth, and then stirred and filtered. In the case where a non-polar solvent is used, it is preferred to dissolve the material to be treated in the non-polar solvent previously, and then add the adsorbent thereto and stir the resulting reaction mixture at 0 to 60° C. for a predetermined time period. The adsorbent is removed in the same manner as stated above, and then the non-polar solvent is removed by distillation. When the more complete removal of the coloring components is required or the material to be decolored has a darker color, it is preferred to repeat the treatment with the adsorbent for several times. In this case, additional any adsorbent may be added after the filtration of the preceding adsorbent and then another round of procedure is performed in the same manner. When a non-polar solvent is used, additional any adsorbent may be added after the proceeding round of addition of an adsorbent, stirring and filtration without the need of removal of the solvent, and then the subsequent round is performed. The solvent is removed after filtration in the final round is completed.

Alternatively, the material given after the molecular distillation may be treated with an acid or alkali prior the treatment with the adsorbent, thereby achieving the decoloration more effectively. In this case, the material to be treated may be dissolved in a non-polar solvent (e.g., hexane) to make the material in a micellar state, and then treated with an acid or alkali. In this step, additional odorous components may be generated or attached to the sterol fatty acid ester. In this case, the treatment with the adsorbent (Step 141) is required to be performed after the molecular distillation (Step 131) and prior to the steam distillation (Step 151).

Once the sterol fatty acid ester (Step 150) without coloring components (Step 142) is obtained, steam distillation (Step 151) is performed as the final, third purification step, to remove odorous components (Step 152) or the like. For use as a food material, the sterol fatty acid ester after the decoloration is required to remove odorous components derived from the starting material or generated in the proceeding steps. When the decoloration is performed using an organic solvent, the organic solvent may remain in the product even after the removal of the solvent. Therefore, the remaining organic solvent must be removed completely. Steam distillation makes it possible to remove the odorous components and the remaining organic solvent in the product. In the steam distillation, any type of apparatus may be used, including those of continuous type, semi-continuous type and batch type. The steam distillation is desirable to perform under the conditions of 13.3 kPa or lower and 50 to 200° C., preferably 1330 Pa or lower and 50 to 150° C. The steam distillation may be repeated for several times.

It is generally known that steam distillation at higher temperatures for the purpose of deodorization markedly accelerates the generation of trans fatty acids. Accordingly, in the second invention, it is important to perform the steam distillation at least at 200° C. or lower, preferably at 150° C. or lower. As stated previously, in order to completely remove the odorous components which cannot be removed only through the steam distillation (Step 151), it is required to perform both of the steam distillation (Step 151) and the molecular distillation (Step 131). In this case, it is important to perform the molecular distillation (Step 131) prior to the steam distillation (Step 151).

The sterol fatty acid ester (Step 160), the end product of the second invention, is almost tasteless, odorless and colorless or pale yellow in color and superior in safety and contains no or little trans fatty acids, and therefore is suitable for a daily food material, a health food material and a pharmaceutical material.

The sterol fatty acid ester has the potential effect of reducing cholesterol level. Accordingly, the addition of the sterol fatty acid ester, as a functional material, to daily food products such as margarine and dressing is considered. According to the second invention, since the end product having a desired melting point can be obtained, such end product is expected the application to wide variety of food products.

The sterol fatty acid ester rich in any fatty acid is also expected to be used in health food products and, in the future in pharmaceuticals, as a new, highly physiologically active material which is contemplated to exert the functions of the fatty acid included therein.

(c) The third aspect of the present invention will be described hereinbelow.

The feature of the third aspect of the present invention (hereinbelow, also referred to as "third invention" for convenience) resides in a production of a highly safe, inexpensive dietary sterol fatty acid ester containing no or little trans fatty acids, from a vegetable oil deodorizer distillate.

Figure 2:
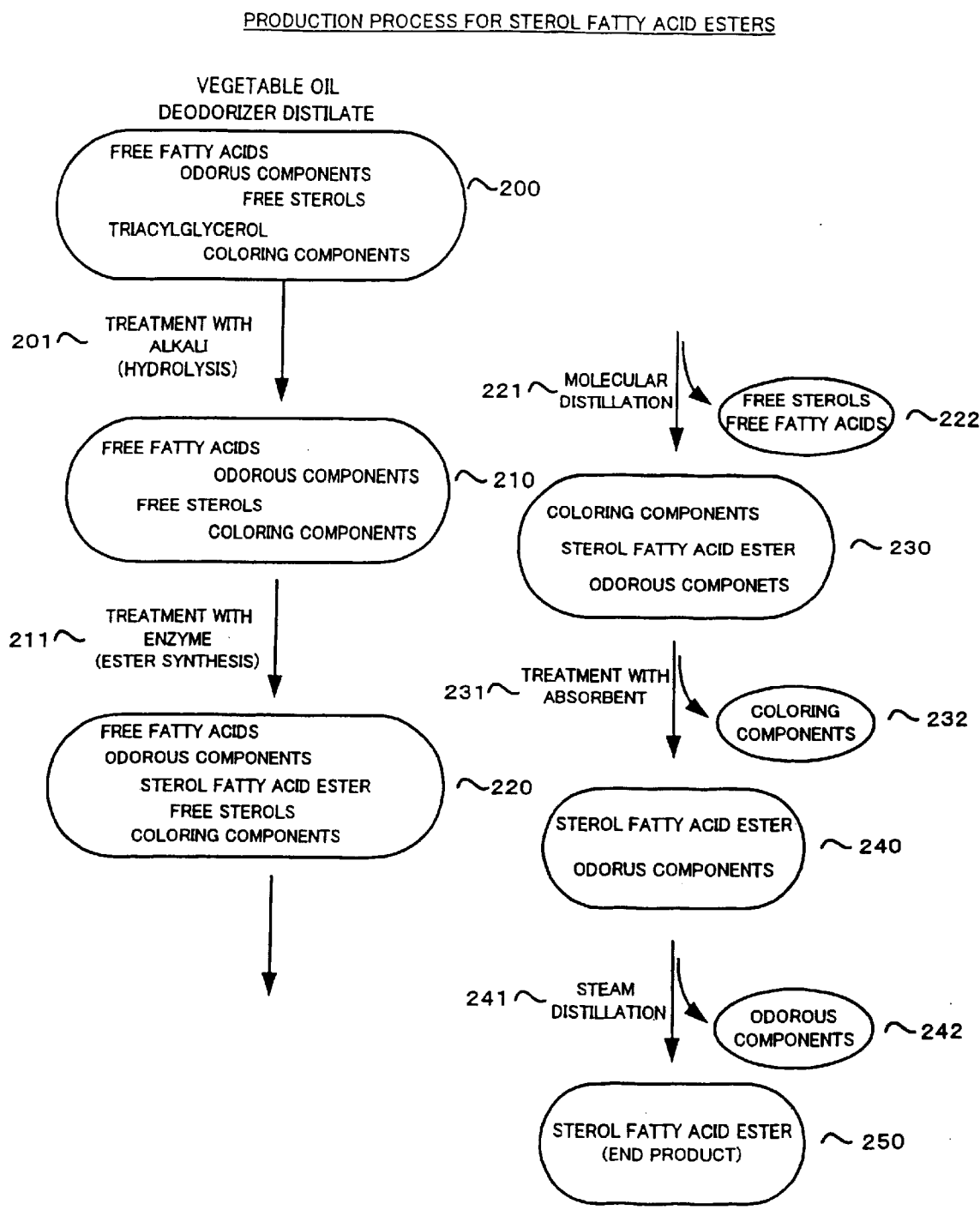
FIG. 2 is a schematic diagram illustrating a process according to the third aspect of the present invention.

The third aspect is schematically described with reference to FIG. 2. A vegetable oil deodorizer distillate (Step 200) is used as a starting material which is produced, as a fraction containing volatile materials, in the deodorization process included in the purification process for a vegetable oil. Fatty acid esters, e.g., triacylglycerols, in the vegetable oil deodorizer distillate are previously degraded by hydrolysis with a chemical catalyst (Steps 201 and 210). Subsequently, the synthetic reaction of a sterol fatty acid ester is performed under strictly controlled conditions using a lipolytic enzyme capable of selectively acting on cis fatty acids (Steps 211 and 220). The resulting sterol fatty acid ester undergoes several steps of purification process (Steps 221, 231 and 241) to afford qualities suitable for a food material, whereby a highly safe, inexpensive dietary sterol fatty acid ester containing no or little trans fatty acids (Step 250) can be produced enzymatically.

(1) According to the third aspect of the present invention is a process for enzymatically producing a dietary sterol fatty acid ester comprising adding a lipolytic enzyme to a mixture of a starting material containing sterols and a fat and oil primarily comprising triacylglycerol to produce a sterol fatty acid ester and then purifying the sterol fatty acid ester in a predetermined purification process, the process comprising:

providing, as a starting material, a vegetable oil deodorizer distillate which is produced in the deodorization process of a vegetable oil performing hydrolysis of fatty acid esters in the vegetable oil deodorizer distillate;

performing a synthetic reaction of a sterol fatty acid ester from the mixture with a lipolytic enzyme capable of selectively acting on cis fatty acids for a predetermined time period under the conditions where temperature and water content are controlled;

as a first purification step, performing molecular distillation to primarily remove unreacted sterols and fatty acids;

as a second purification step, treating the resulting product with an adsorbent to primarily remove coloring components; and then as a third purification step, performing steam distillation to primarily remove odorous components, the sterol fatty acid ester being superior in flavor properties and safety.

(2) In the item (1), soybean oil deodorizer distillate which is produced in the refining process of soybean oil may be used as the starting material.

(3) In the item (1), the hydrolysis may be performed using an acidic or alkaline catalyst.

(4) In the item (1), the synthetic reaction of a sterol fatty acid ester may be performed using a lipolytic enzyme capable of selectively acting on cis fatty acids which is originated from a microorganism of the genus Candida or Mucor.

(5) In the item (1), the synthetic reaction of a sterol fatty acid ester may be performed at 30 to 60° C. within 48 hours in the presence of water of 0.1 to 50 wt % based on the weight of the starting material.

(6) In the item (1), the molecular distillation as the first purification step may be performed at 13.3 Pa or lower and 100 to 250° C.

(7) In the item (1), the treatment with an adsorbent as the second purification step may be performed at 100° C. or lower using, as the adsorbent, activated clay, silica gel, activated carbon or a mixture of two or more of them in an amount of 0.1 to 50 wt % based on the weight of the material to be treated.

(8) In the item (1), the steam distillation as the third purification step may be performed at 1330 Pa or lower and 50 to 150° C.

(9) In the item (1), the end product sterol fatty acid ester may have a sterol fatty acid ester content of 90 wt % or more, a trans fatty acid content in the constitutive fatty acids of 2 wt % or lower, a peroxide value of 10 or lower, an acid value of 1 or lower and a Gardner color scale of 6 or lower and may be almost odorless as determined by a sensory test.

The third aspect of the present invention is described in detail hereinbelow with reference to FIG. 2.

In the third invention, the vegetable oil deodorizer distillate (Step 200) used as a starting material is any one derived from any plant oil, as long as it is produced in the deodorization process for a vegetable oil. Examples of the vegetable oil deodorizer distillate include those of soybean oil, rapeseed oil, palm oil, sunflower seed oil, rice bran oil, corn oil, safflower oil.

Since the specific examples of the vegetable oil deodorizer distillate are the same as those in the first and second aspects of the present invention, overlapped descriptions are omitted.

Among the fatty acids, particularly in linolenic acid which contains relatively many unsaturated bonds, a trans-type one constitutes a high proportion. Therefore, soybean oil deodorizer distillate which is rich in linolenic acid may have a high trans fatty acid content.

The vegetable oil deodorizer distillate may be used in the untreated form. However, since it usually contains coloring components and other solid materials, it is preferably used after the removal of unnecessary components such solid materials for example by use of an adsorbent or filtration. If cost permits, it may be preferred to previously concentrate the free sterols and fatty acids in the vegetable oil deodorizer distillate for example by distillation or fractionation. Alternatively, additional free sterols and free fatty acids may be added to the vegetable oil deodorizer distillate.

The advantage of the third invention is that both sterols and fatty acids, i.e., base components for the synthesis of a sterol fatty acid ester, are already present in the starting material, i.e., the vegetable oil deodorizer distillate. Use of such a vegetable oil deodorizer distillate as the starting material makes it possible to produce a sterol fatty acid ester at low cost.

However, if a chemical catalyst or a lipolytic enzyme having no selective activities is used to synthesize a sterol fatty acid ester, then trans fatty acid as stated above may also be utilized as the base material for the synthesis. As a result, the end product may contain trans fatty acids which are not desirable for food product from a safety viewpoint.

In the third invention, fatty acid esters, e.g., triacylglycerol, in the vegetable oil deodorizer distillate are previously hydrolyzed (Steps 201 and 210). Subsequently, the synthesis of a sterol fatty acid ester is performed without utilizing trans fatty acids in the vegetable oil deodorizer distillate as the base material by using a lipolytic enzyme which does not act or hardly acts on trans fatty acids, i.e., a lipolytic enzyme capable of selectively acting on cis fatty acids (Steps 211 and 220). In this manner, a product containing no or little trans fatty acids can be produced at low cost.

The catalyst to be used in the hydrolysis of the fatty acid esters, i.e., triacylglycerol, in the vegetable oil deodorizer distillate may be any one as long as it is available for food products, such as a chemical catalyst, e.g., an acid and an alkali. The catalyst includes an acid such as hydrochloric acid and sulfuric acid; and an alkali such as sodium hydroxide and potassium hydroxide (Step 201).

Generally for the hydrolysis of the fatty acid esters, a lipolytic enzyme such as a lipase may also be used in place of a chemical catalyst. When a lipolytic enzyme is used in the hydrolysis of the fatty acid esters in the vegetable oil deodorizer distillate, however, a synthesis of a sterol fatty acid ester may proceed concurrently with the degradation of triacylglycerol and so on. For this reason, it is improper to use a lipolytic enzyme, e.g., a lipase, in the hydrolysis of the fatty acid esters.

In the hydrolysis of the fatty acid esters, any catalyst concentration, any reaction temperature and any reaction time may be employed. However, it is preferred to perform the reaction at 150° C. or lower within several hours, since an excess reaction may cause undesirable phenomena such as deterioration of every components in the vegetable oil deodorizer distillate and coloration of the resulting product.

After the synthetic reaction is completed, the neutralization is performed with a suitable acid or alkali, followed by washing with water to remove glycerin, salts and so on which may be produced in the synthesis and the chemical catalyst. After washing with water, resulting product is subjected to aqueous/oily phase separation and then heated at about 60 to 120° C. for a predetermined time period under reduced pressure to remove water therefrom.

Once the components of Step 210 are obtained, the synthetic reaction of a sterol fatty acid ester is then performed using a lipolytic enzyme capable of selectively acting on cis fatty acids (Steps 211 and 220).

The lipolytic enzyme which selectively acts on cis fatty acids includes those enzymes originated from various microorganisms of the genera Candida, Mucor, Rhizopus, Aspergillus and Humicola, and particularly preferred enzymes are those enzymes originated from *Candida cylindracea, Aspergillus niger, Aspergillus oryzae, Humicola lanuginosa, Rhizopus miehei, Rhizopus delemar* and *Rhizopus arrhizus*.

When the synthetic reaction is performed under high temperature conditions, a thermostable lipolytic enzyme may be used. The enzyme may be used in the purified or partially purified form. In the case where a lipolytic enzyme originated from a microorganism, microorganism cell bodies or a culture of the microorganism may also be used. The enzyme may also be in the free state or be immobilized onto any of various supports such as cerite.

The conditions to be employed for the synthetic reaction of the sterol fatty acid ester with a lipolytic enzyme should be controlled strictly so that a sterol fatty acid ester having qualities suitable for a food material such as flavor properties, e.g., color, odor and taste, and safety can be produced at low cost. The conditions of the synthetic reaction are described in the following.

The enzyme may be used in an amount of 50,000 units (U) or less, preferably 10,000 units (U) or less, per gram of the sterols. To avoid the deterioration of the enzyme caused by the treatment under heating in the production process and to produce the end product at low cost, it is desirable to use the enzyme in a smallest possible amount, preferably in an amount of 5,000 units or less per gram of sterols in the starting material. The enzyme may also be added in a step-wise manner during the synthetic reaction to reduce the amount of the enzyme.

In the third invention, in the presence of no water or an extremely small amount of water, triacylglycerol or a trace amount of diacylglycerol or monoacylglycerol may still remain in the product, which is hardly removed in the subsequent purification process. Therefore, it is preferred to perform the enzymatic reaction in the presence of 0.1 wt % or more of water. In this case, triacylglycerol and co-existing diacylglycerol, monoacylglycerol and so on undergo hydrolysis into free fatty acids and glycerin. The fatty acids produced by this hydrolysis can also be utilized as the starting material for the synthetic reaction of the sterol fatty acid ester.

The efficiency of the synthetic reaction is more enhanced, the more water is added. However, the water added must be removed in the purification process after the synthesis of the sterol fatty acid ester. Therefore, the amount of water should be minimized for reduction in production cost, and is preferably 300% or less based on the weight of the vegetable oil deodorizer distillate, i.e., the starting material.

To minimize the thermal degradation of the product during the synthetic reaction, the reaction is preferably performed at a lower temperature for a shorter time period, usually at 30 to 60° C. within 48 hours. When the synthesis is performed at a lower temperature, a lipolytic enzyme which can readily exert its enzymatic activity at such a lower temperature may be used.

As in the case of the first and second invention, because of their very high melting points, sterols (one base material) tend to have poor compatibility with fatty acids, i.e., the other base material. Therefore, in some cases, the efficiency of the synthetic reaction of the sterol fatty acid ester may become low. To overcome this problem, the synthetic reaction is performed at a higher temperature, preferably at 50 to 90° C. within 24 hours using a thermostable lipolytic enzyme. In this case, however, thermal deterioration of the sterol fatty acid ester may proceed more aggressively or the enzyme may be inactivated during the reaction. Therefore, a substance having anti-oxidant effect, e.g., Vitamin E and tea polyphenol, may be added to prevent the thermal or oxidative deterioration of the sterol fatty acid ester, and a substance capable of inhibiting the inactivation of an enzyme, e.g., a salt such as bile salt, a carbohydrate and a protein, may be added to prevent the inactivation of the enzyme.

To enhance the efficiency of the synthetic reaction, the reaction is usually performed while stirring the reaction materials, but optionally may be performed in a static state. When the reaction is performed in a static state, an emulsifying agent or the like may be added. An organic solvent such as hexane may also be used to enhance the efficiency of the reaction. In this case, however, the solvent must be removed, which may increase the production cost.

After the synthetic reaction of the sterol fatty acid ester is completed, inactivation of the enzyme, dehydration and removal of the enzyme protein are performed. The inactivation of the enzyme is achieved by stirring the reactants at 60 to 100° C. for about 30 to 120 min. The dehydration is performed by treating the reactant at 60 to 120° C. for a predetermined time period under reduced pressure. The removal of the enzyme protein can be achieved by filtration using a conventional filter paper, filter cloth or any other type of filtration means. If the removal of the enzyme protein is insufficient, then deterioration in quality such as coloration of the sterol fatty acid ester may be caused by the heating in subsequent processes. Therefore, the enzyme protein must be removed completely. For more effective removal, it is preferred to previously add a filter aid, e.g., diatom earth, and then stirred and filtered.

Next, the purification process (Step 221 through the last step) for the sterol fatty acid ester is explained.

In the third invention, in order to produce a sterol fatty acid ester having qualities suitable for a food material, e.g., color, odor and taste, and superior in safety at low cost, the purification of the product given by the synthetic reaction should be performed carefully. Particularly when the purification is performed at high temperatures, generation of trans fatty acids and peroxides may occur. Therefore, the temperature conditions must be controlled strictly.

As a first purification step, a molecular distillation (Step 221) is performed to primarily remove the unreacted sterols and fatty acids (Step 222). The sterol fatty acid ester, i.e., reaction product, given after the removal of the enzyme protein of Step 220 contains various impurities including unreacted sterols and fatty acids and other trace components, and these impurities must be removed.

In the third invention, molecular distillation (Step 221) is first performed to efficiently remove sterols and fatty acids. The sterol fatty acid ester is given as a residue (Step 230), while unreacted sterols and fatty acids and parts of odorous components are removed as a distillate. The apparatus for the molecular distillation may be of falling film type, centrifugal type or any other type of short pass distillation apparatus. Any apparatus may be used as long as it can achieve the desired vacuum pressure and temperature and can remove the desired free sterols, free fatty acids and other trace components.

The molecular distillation is preferably performed at 133 Pa or lower and 100 to 300° C., more preferably at 13.3 Pa or lower and 100 to 250° C. The molecular distillation may be performed repeatedly for several times. In this step, it is possible to remove odorous components which cannot be removed in the steam distillation (Step 241), i.e., the third step of the purification process. On the other hand, some heating odor may be generated in this step. In this case, additional molecular distillation (Step 221) is required prior to the steam distillation (Step 241) to produce the end product without odorous components efficiently.

Subsequently, as a second purification step (Step 231), coloring components (Step 232) are primarily removed.

The sterol fatty acid ester after the molecular distillation (Step 230) contains coloring components derived from the starting material and coloring components resulting from the heating during the distillation, as well as odorous components. In the third invention, to remove the coloring components efficiently, the sterol fatty acid ester is treated with an adsorbent (Step 231).

The adsorbent includes those adsorbent conventionally used for purification of fats and oils, such as activated clay, acidic clay, activated carbon, silica, silica-magnesia and so on, and is preferably activated clay, activated carbon or silica. These may be used singly or in combination. The adsorbent is preferably added in an amount of 0.1 to 50 wt %, more preferably 1 to 20 wt %, based on the weight of the sterol fatty acid ester to be treated. For more efficient decoloration, it is preferred to perform the treatment with the adsorbent in a non-polar solvent such as hexane. The solvent is preferably used in 0.1 to 50 volumes, more preferably 0.5 to 20 volumes, of the material to be treated. When a non-polar solvent is not used, the decoloration is performed by adding the adsorbent to the material to be treated and then stirring at 40 to 150° C. for a predetermined time period. This procedure may be performed under normal atmospheric pressure. However, to prevent the deterioration of the material to be treated and decolor it more effectively, the procedure is preferably performed under reduced pressure. A lower pressure is preferred, such as 13.3 kPa or lower.

After the treatment, the adsorbent is removed by filtration using any conventional filtrating means, such as a filter paper, a filter cloth or any other filtration means. For more effective removal, it is preferred to previously add a filter aid (e.g., diatom earth), and then stirred and filtered. The reaction mixture is then stirred and filtrated, thereby achieving the removal of the adsorbent more effectively. In the case where a non-polar solvent is used, it is preferred to dissolve the material to be treated in the non-polar solvent previously, and then add the adsorbent thereto and stir the resulting reaction mixture at 0 to 60° C. for a predetermined time period. The adsorbent is removed in the same manner as stated above, and then the non-polar solvent is removed by distillation. When the more complete removal of the coloring components is required or the material to be decolored has a darker color, it is preferred to repeat the treatment with the adsorbent for several times. In this case, additional any adsorbent may be added after the filtration of the preceding adsorbent and then another round of procedure is performed in the same manner. When a non-polar solvent is used, additional any adsorbent may be added after the proceeding round of addition of an adsorbent, stirring and filtration without the need of removal of the solvent, and then the subsequent round is performed. The solvent is removed after filtration in the final round is completed.

Alternatively, the material given after the molecular distillation may be treated with an acid or alkali prior the treatment with the adsorbent, thereby achieving the decoloration more effectively. In this case, the material to be treated may be dissolved in a non-polar solvent, e.g., hexane, to make the material in a micellar state, and then treated with an acid or alkali.

In this step, additional odorous components may be generated or attached to the sterol fatty acid ester. In this case, the treatment with the adsorbent (Step 231) is required to be performed after the molecular distillation (Step 221) and prior to the steam distillation (Step 241).

As the final, third purification step, steam distillation (Step 241) is performed to remove odorous components (Step 242) or the like. For use as a food material, the sterol fatty acid ester after the decoloration is required to remove odorous components derived from the starting material or generated in the proceeding steps. When the decoloration is performed using an organic solvent, the organic solvent may remain in the product even after the removal of the solvent. Therefore, the remaining organic solvent must be removed completely. Steam distillation (Step 241) makes it possible to remove the odorous components and the remaining organic solvent in the product.

In the steam distillation, any type of apparatus may be used, including those of continuous type, semi-continuous type and batch type. The steam distillation is desirable to perform under the conditions of 13.3 kPa or lower and 50 to 200° C., preferably 13.3 kPa or lower and 50 to 150° C. The steam distillation may be repeated for several times.

It is generally known that steam distillation at higher temperatures for the purpose of deodorization markedly accelerates the generation of trans fatty acids. Accordingly, in the third invention, it is important to perform the steam distillation at least at 200° C. or lower, preferably at 150° C. or lower. As stated previously, in order to completely remove the odorous components which cannot be removed only through the steam distillation, it is required to perform both of the steam distillation and the molecular distillation. In this case, it is important to perform the molecular distillation prior to the steam distillation.

The sterol fatty acid ester (Step 250), the end product of the third invention, is almost tasteless, odorless and colorless or pale yellow in color and has a reduced trans fatty acid content and superior safety, and therefore is suitable for a daily food material, a health food material and a pharmaceutical material. The sterol fatty acid ester has the potential effect of reducing cholesterol level. Accordingly, the sterol fatty acid ester is expected to be used, as a functional material, in daily food products, e.g., margarine and dressing, and health food products and, in the future, in pharmaceuticals.

DESCRIPTION OF THE PREFERRED EMBODIMENTS

The present invention will be described more in detail by way of the following examples. The present invention, however, is not limited to these specific examples.

(A) Examples of the first aspect of the present invention will be described hereinbelow.

EXAMPLE 1

Soybean oil deodorizer distillate (sterol content: 13 wt %) (200 g) was added with water (100 g), and lipase powder originated from a microorganism of the genus Candida (360,000 units/g: "Lipase OF", a product by Meito Sangyo Co., Ltd.) (2.0 g) was further added thereto while stirring at 40° C. The resulting mixture was allowed to react at 40° C. for 24 hours while stirring. The reaction mixture was heated to 80° C. and stirred at that temperature for 30 min. to inactivate the enzyme. The reaction product was dehydrated at 80° C. under reduced pressure. The resulting product was added with diatom earth (1.0 g), stirred, and then filtered to remove the enzyme protein. The resultant product was subjected to molecular distillation using a centrifugal molecular distillation apparatus at a vacuum pressure of 1.5 Pa, an evaporating surface temperature of 230° C. and a flow rate of 2.0 l/hr to give a sterol fatty acid ester without impurities including free fatty acids (33 g). For the treatment with an adsorbent, the sterol fatty acid ester was dissolved in five volumes (based on the residue) of hexane, added with 20 wt % (based on the residue) of activated clay, and then stirred at room temperature for 30 min. The resulting solution was filtered to remove the activated clay having coloring components adsorbed thereon, and the filtrate was evaporated using an evaporator to remove the solvent, thereby giving the sterol fatty acid ester without coloring components (27 g). Finally, the sterol fatty acid ester was subjected to steam distillation using a batch-type steam distillation apparatus under the condition of a vacuum pressure of 500 Pa, a distillation temperature of 150° C. and a distillation time of 2 hours, thereby giving the sterol fatty acid ester without odorous components (26 g) as the end product. The sterol fatty acid ester was almost tasteless, odorless and pale yellow in color. The analytic results are shown in Table 1.

The sterol fatty acid ester was mixed with soybean oil in an amount of 100 wt % based on the weight of the sterol fatty acid ester, and a product having good fluidity was obtained.

EXAMPLE 2

Soybean oil deodorizer distillate (sterol content: 13 wt %) (200 g) was added with water (50 g), and thermostable lipase powder originated from a microorganism of the genus Rhizopus (10,000 units/g; "Talipase", a product by Tanabe Seiyaku Co., Ltd.) (3.0 g) was further added thereto while stirring at 40° C. The resulting mixture was allowed to react at 50° C. for 24 hours while stirring. The reaction mixture was heated to 90° C. and stirred at that temperature for 30 min. to inactivate the enzyme. The product was dehydrated at 80° C. under reduced pressure. The resulting product was added with diatom earth (1.0 g), stirred, and then filtered to remove the enzyme protein. The resultant product was subjected to molecular distillation using a centrifugal molecular distillation apparatus at a vacuum pressure of 1.5 Pa, an evaporating surface temperature of 230° C. and a flow rate of 2.0 l/hr to give a sterol fatty acid ester without impurities including free fatty acids (31 g). For the treatment with an adsorbent, the sterol fatty acid ester was dissolved in five volumes (based on the residue) of hexane, added with 20 wt % (based on the residue) of silica gel, and then stirred at room temperature for 30 min. The resulting solution was filtered to remove the silica gel having coloring components adsorbed thereon, and the filtrate was evaporated using an evaporator to remove the solvent, thereby giving the sterol fatty acid ester without coloring components (25 g). Finally, the sterol fatty acid ester was subjected to steam distillation using a batch-type steam distillation apparatus under the conditions of a vacuum pressure of 500 Pa, a distillation temperature of 150° C. and a distillation time of 2 hours, thereby giving the sterol fatty acid ester without odorous components (24 g) as the end product. The sterol fatty acid ester was almost tasteless, odorless and pale yellow in color. The analytic results are shown in Table 1.

EXAMPLE 3

Rapeseed vegetable oil deodorizer distillate (sterol content: 8 wt %) (200 g) was added with water (100 g), and lipase powder originated from a microorganism of the genus Candida (360,000 units/g: "Lipase OF", a product by Meito Sangyo Co., Ltd.) (2.0 g) was further added thereto while stirring at 40° C. The resulting mixture was allowed to react at 40° C. for 24 hours while stirring. The reaction mixture was heated to 80° C. and stirred at that temperature for 30 min. to inactivate the enzyme. The reaction product was dehydrated at 80° C. under reduced pressure. The resulting product was added with diatom earth (1.0 g), stirred, and then filtered to remove the enzyme protein. The resultant product was subjected to molecular distillation using a centrifugal molecular distillation apparatus at a vacuum pressure of 1.5 Pa, an evaporating surface temperature of 230° C. and a flow rate of 2.0 l/hr to give a sterol fatty acid ester without impurities including free fatty acids (28 g). For the treatment with an adsorbent, the sterol fatty acid ester was dissolved in five volumes (based on the residue) of hexane, added with 20 wt % (based on the residue) of activated carbon, and then stirred at room temperature for 30 min. The resulting solution was filtered to remove the activated carbon having coloring components adsorbed thereon, and the filtrate was evaporated using an evaporator to remove the solvent, thereby giving the sterol fatty acid ester without coloring components (22 g). Finally, the sterol fatty acid ester was subjected to steam distillation using a batch-type steam distillation apparatus under the condition of a vacuum pressure of 500 Pa, a distillation temperature of 150° C. and a distillation time of 1 hour, thereby giving the sterol fatty acid ester without odorous components (21 g) as the end product. The sterol fatty acid ester was almost tasteless, odorless and pale yellow in color. The analytic results are shown in Table 1.

EXAMPLE 4

Palm vegetable oil deodorizer distillate (sterol content: 11 wt %) (200 g) was added with water (100 g), and lipase powder originated from a microorganism of the genus Candida (360,000 units/g: "Lipase OF", a product by Meito Sangyo Co., Ltd.) (2.0 g) was further added thereto while stirring at 40° C. The resulting mixture was allowed to react at 40° C. for 24 hours while stirring. The reaction mixture was heated to 80° C. and stirred at that temperature for 30 min. to inactivate the enzyme. The reaction product was dehydrated at 80° C. under reduced pressure. The resulting product was added with diatom earth (1.0 g), stirred, and then filtered to remove the enzyme protein. The resultant product was subjected to molecular distillation using a centrifugal molecular distillation apparatus at a vacuum pressure of 1.5 Pa, an evaporating surface temperature of 230° C. and a flow rate of 2.0l/hr to give a sterol fatty acid ester without impurities including free fatty acids (32 g). For the treatment with an adsorbent, the sterol fatty acid ester was dissolved in five volumes (based on the residue) of hexane, added with 20 wt % (based on the residue) of activated clay, and then stirred at room temperature for 30 min. The resulting solution was filtered to remove the activated clay having coloring components adsorbed thereon, and the filtrate was evaporated using an evaporator to remove the solvent, thereby giving the sterol fatty acid ester without coloring components (21 g). Finally, the sterol fatty acid ester was subjected to steam distillation using a batch-type steam distillation apparatus under the conditions of a vacuum pressure of 500 Pa, a distillation temperature of 150° C. and a distillation time of 1 hour, thereby giving the sterol fatty acid ester without odorous components (20 g) as the end product. The sterol fatty acid ester was almost tasteless, odorless and pale yellow in color. The analytic results are shown in Table 1.

COMPARATIVE EXAMPLE 1

A soybean-derived sterol (sterol content: 95 wt %) (100 g) was mixed with linolenic acid (linolenic acid content: 97%) (200 g), and then lipase powder originated from a microorganism of the genus Candida (360,000 units/g: "Lipase OF", a product by Meito Sangyo Co., Ltd.) (2.0 g) was further added thereto while stirring at 40° C. The resulting mixture was subjected to synthetic reaction at 40° C. for 36 hours while stirring, followed by molecular distillation using a falling film molecular distillation apparatus and then treatment with activated carbon, thereby giving a sterol fatty acid ester (68 g). The sterol fatty acid ester had a characteristic pungent odor and was brown in color. The analytic results are shown in Table 1.

COMPARATIVE EXAMPLE 2

A soybean-derived sterol (sterol content: 95 wt %) (100 g) was mixed with linolenic acid (linolenic acid content: 97%) (200 g), and then lipase powder originated from a microorganism of the genus Candida (360,000 units/g: "Lipase OF", a product by Meito Sangyo Co., Ltd.) (2.0 g) was further added thereto while stirring at 40° C. The resulting mixture was subjected to synthetic reaction at 40° C. for 24 hours while stirring, followed by inactivation of the enzyme, dehydration and removal of the enzyme protein. The product was subjected to molecular distillation using a centrifugal molecular distillation apparatus. The residue was added with five volumes of hexane and 20 wt % of activated carbon and then stirred. Finally, the resulting product was subjected to steam distillation to give a sterol fatty acid ester (59 g). The sterol fatty acid ester was almost tasteless, odorless and pale yellow in color. However, the starting material was very expensive compared with that used in Example 1 and, therefore, the production cost was over 10 times higher than that of Example 1. The analytic results are shown in Table 1.

In Examples 1 to 4, since an inexpensive vegetable oil deodorizer distillate such as soybean oil deodorizer distillate, rapeseed vegetable oil deodorizer distillate and palm vegetable oil deodorizer distillate is used as the starting material, the production cost can be reduced to a great extent. In addition, as shown in Table 1, a sterol fatty acid esters with almost tasteless and odorless and pale yellow in color which have a peroxide value of 15 or lower, an acid value of 3 or lower and a Gardner color scale of 8 or lower can be produced.

In Comparative Example 1, on the contrary, a soybean-derived sterol and linolenic acid are used as the starting materials, and are treated by esterification reaction followed by molecular distillation and treatment with an adsorbent. The cost of the raw materials is expensive, and the sterol fatty acid ester as the end product has a characteristic pungent odor and brown color, which is not appropriate as a food material.

In Comparative Example 2, a soybean-derived sterol and linolenic acid are used as the starting materials, and are treated in the same manner as in Example 1. Although the sterol fatty acid ester as the end product is tasteless, odorous and pale yellow in color and therefore is suitable as a food material, the production cost is over 10 times higher than that of Example 1. Accordingly, Comparative Example 2 is largely impractical compared with Examples 1 to 4.

TABLE 1

|  | Ex. 1 | Ex. 2 | Ex. 3 | Ex. 4 | C. Ex. 1 | C. Ex. 2 |
|---|---|---|---|---|---|---|
| Sterol fatty acid ester content (wt %) | 94.2 | 92.8 | 92.7 | 91.9 | 90.4 | 92.4 |
| Peroxide value | 3.2 | 6.4 | 4.7 | 2.9 | 18.2 | 2.8 |
| Acid value | 0.2 | 0.6 | 0.4 | 0.4 | 2.6 | 0.9 |
| Color (Gardner) | 4− | 5− | 5+ | 4− | 9+ | 5+ |
| Odor | almost odorless | almost odorless | almost odorless | almost odorless | characteristic pungent odor | almost odorless |

(B) Examples of the second aspect of the present invention will be described hereinbelow.

EXAMPLE 5

Soybean oil deodorizer distillate (sterol content: 12.3 wt %) (200 g) was added with a 0.2N solution of potassium hydroxide (KOH) in ethanol (10 ml), and stirred at 60° C. for 2 hours to hydrolyze fatty acid esters including triacylglycerol. The reaction solution was neutralized with 0.4N hydrochloric acid, washed with water to remove ethanol, KCl, KOH and glycerin, and then subjected to dehydration at 80° C. under reduced pressure. The resulting product was subjected to molecular distillation using a centrifugal molecular distillation apparatus at a vacuum pressure of 1.5 Pa and an evaporating surface temperature of 170° C. to primarily remove fatty acids as a distillate and collect the residue as a sterol-containing fraction (28 g).

The sterol-containing fraction (25 g) was mixed with purified soybean oil (50 g), and a suspension of lipolytic enzyme powder originated from a microorganism of the genus Pseudomonas (50,000 units/g: "Lipase TL", a product by Meito Sangyo Co., Ltd.) (1.0 g) in water (25 ml) was further added thereto. The resulting mixture was subjected to a synthetic reaction of a sterol fatty acid ester at 40° C. for 24 hours while stirring. The reaction solution was heated to 80° C. and stirred at that temperature for 30 min. to inactivate the enzyme. The reaction product was washed with hot water, dehydrated at 80° C. under reduced pressure, added with diatom earth (1.0 g), stirred, and then filtered to remove the enzyme protein.

As the first purification step, the resulting product was subjected to molecular distillation using a centrifugal molecular distillation apparatus at a vacuum pressure of 1.5 Pa and an evaporating surface pressure of 230° C. to remove unreacted fatty acids and sterols as a distillate. As the second purification step, the residue containing a sterol fatty acid ester was added with activated clay in an amount of 10 wt % based on the weight of the residue. The mixture was stirred at 80° C. for 30 min. under reduced pressure and then filtered to remove the activated clay having coloring components adsorbed thereon. Finally, as the third purification step, the resulting product was subjected to steam distillation under conditions of a vacuum pressure of 500 Pa, a distillation temperature of 150° C. and a distillation time of 1 hour, thereby giving a sterol fatty acid ester without odorous components (34 g) as the end product.

The sterol fatty acid ester was almost tasteless, odorless and pale yellow in color, and had a melting point of 30.1° C. and a trans fatty acid content in the constitutive fatty acids of 1.2 wt %. The analytic results are shown in Table 2.

EXAMPLE 6

A product given by the same hydrolysis procedure with potassium hydroxide in ethanol as in Example 5 was subjected to molecular distillation using a centrifugal molecular distillation apparatus at a vacuum pressure of 1.5 Pa and an evaporating surface temperature of 170° C. to primarily remove fatty acids as a distillate and collect the residue as a sterol-containing fraction. The sterol-containing fraction was subjected to additional molecular distillation at a vacuum pressure of 1.5 Pa and an evaporating surface temperature of 230° C., thereby giving a sterol-containing fraction as a distillate (22 g).

The sterol-containing fraction (20 g) was mixed with purified soybean oil (40 g), and a suspension of lipolytic enzyme powder originated from a microorganism of the genus Alcaligenes (90,000 units/g: "Lipase PC", a product by Meito Sangyo Co., Ltd.) (0.4 g) in water (20 ml) was further added thereto. The resulting mixture was subjected to a synthetic reaction of a sterol fatty acid ester at 40° C. for 24 hours while stirring. The reaction solution was subjected to enzyme inactivation, washing with hot water, dehydration and removal of enzyme protein in the same manner as in Example 1.

The resulting product was subjected to molecular distillation (i.e., the first purification step) treatment with an adsorbent (i.e., the second purification step) and steam distillation (i.e., the third purification step) in the same manner as in Example 5, thereby giving a sterol fatty acid ester (29 g).

The sterol fatty acid ester was almost tasteless, odorless and almost colorless and had a melting point of 31.5° C. and a trans fatty acid content in the constitutive fatty acids of 1.3 wt %. The analytic results are shown in Table 2.

EXAMPLE 7

A sterol-containing fraction (25 g) collected in the same manner as in Example 5 was mixed with purified rapeseed oil (50 g), and a suspension of lipolytic enzyme powder originated from a microorganism of the genus Mucor (80,000 units/g) (0.5 g) in water (25 ml) was further added thereto. The resulting mixture was subjected to a synthetic reaction of a sterol fatty acid ester at 40° C. for 24 hours while stirring. The reaction solution was subjected to enzyme inactivation, washing with hot water, dehydration and removal of enzyme protein in the same manner as in Example 1.

The resulting product was subjected to molecular distillation (i.e., the first purification step) treatment with an adsorbent (i.e., the second purification step) and steam distillation (i.e., the third purification step) in the same manner as in Example 5, thereby giving a sterol fatty acid ester (35 g).

The sterol fatty acid ester was almost tasteless, odorless and pale yellow in color, and had a melting point of 31.2° C. and a trans fatty acid content in the constitutive fatty acids of 1.0 wt %. The analytic results are shown in Table 2.

EXAMPLE 8

A sterol-containing fraction (25 g) collected in the same manner as in Example 5 was mixed with purified olive oil (50 g), and a suspension of lipolytic enzyme powder originated from a microorganism of the genus Candida (360,000 units/g: "Lipase OF", a product by Meito Sangyo Co., Ltd.) (0.2 g) in water (25 ml) was further added thereto. The resulting mixture was subjected to a synthetic reaction of a sterol fatty acid ester at 40° C. for 24 hours while stirring. The reaction solution was subjected to enzyme inactivation, washing with hot water, dehydration and removal of enzyme protein in the same manner as in Example 5.

The resulting product was subjected to molecular distillation (i.e., the first purification step) treatment with an adsorbent (i.e., the second purification step) and steam distillation (i.e., the third purification step) in the same manner as in Example 5, thereby giving a sterol fatty acid ester (36 g).

The sterol fatty acid ester was almost tasteless, odorless and pale yellow in color, and had a melting point of 34.7° C. and a trans fatty acid content in the constitutive fatty acids of 0.4 wt %. The analytic results are shown in Table 2.

EXAMPLE 9

A sterol-containing fraction (25 g) collected in the same manner as in Example 5 was mixed with purified palm oil (50 g), and a suspension of lipolytic enzyme powder originated from a microorganism of the genus Rhizopus (60,000 units/g: "Talipase", a product by Tanabe Seiyaku Co., Ltd.) (0.5 g) in water (25 ml) was further added thereto. The resulting mixture was subjected to a synthetic reaction of a sterol fatty acid ester at 60° C. for 12 hours while stirring. The reaction solution was subjected to enzyme inactivation, washing with hot water, dehydration and removal of enzyme protein in the same manner as in Example 5.

The resulting product was subjected to molecular distillation (i.e., the first purification step), treatment with an adsorbent (i.e., the second purification step) and steam distillation (i.e., the third purification step) in the same manner as in Example 5, thereby giving a sterol fatty acid ester (32 g).

The sterol fatty acid ester was almost tasteless, odorless and pale yellow in color, and had a melting point of 68.5° C. and a trans fatty acid content in the constitutive fatty acids of 0.2 wt %. The analytic results are shown in Table 2.

EXAMPLE 10

A sterol-containing fraction (25 g) collected in the same manner as in Example 5 was mixed with purified tuna oil (50 g), and a suspension of lipolytic enzyme powder originated from a microorganism of the genus Mucor (80,000 units/g) (0.5 g) in water (25 ml) was further added thereto. The resulting mixture was subjected to a synthetic reaction of a sterol fatty acid ester at 40° C. for 24 hours while stirring. The reaction solution was subjected to enzyme inactivation, washing with hot water, dehydration and removal of enzyme protein in the same manner as in Example 5.

The resulting product was subjected to molecular distillation (i.e., the first purification step), treatment with an adsorbent (i.e., the second purification step) and steam distillation (i.e., the third purification step) in the same manner as in Example 5, thereby giving a sterol fatty acid ester (35 g).

The sterol fatty acid ester was almost tasteless, odorless and pale yellow in color, and had a melting point of 15.1° C. and a trans fatty acid content in the constitutive fatty acids of 1.8 wt %. The analytic results are shown in Table 2.

COMPARATIVE EXAMPLE 3

The same soybean oil deodorizer distillate (sterol content: 12.3 wt %) as used in Example 5 (200 g) was added with a suspension of lipolytic enzyme powder originated from a microorganism of the genus Pseudomonas (50,000 units/g) (4.0 g). The resulting mixture was subjected to a synthetic reaction of a sterol fatty acid ester at 40° C. for 48 hours while stirring. The reaction solution was washed with hot water, dehydrated at 100° C. and then filtered to remove the enzyme protein.

The resulting product was subjected to molecular distillation using a centrifugal molecular distillation apparatus at a vacuum pressure of 1.5 Pa and an evaporating surface temperature of 230° C., thereby giving a sterol fatty acid ester (43 g). The sterol fatty acid ester had very strong bitter taste and strong fetid odor and brown color. It had a melting point of 29.80° C., a trans fatty acid content in the constitutive fatty acids of 4.8 wt % and a sterol fatty acid ester content of 59.2 wt %. The analytic results are shown in Table 3.

COMPARATIVE EXAMPLE 4

The same soybean oil deodorizer distillate (sterol content: 12.3 wt %) as used in Example 5 (200 g) was added with a suspension of lipolytic enzyme powder originated from a microorganism of the genus Alcaligenes (90,000 units/g: "Lipase PL", a product by Meito Sangyo Co., Ltd.) (0.6 g). The resulting mixture was subjected to a synthetic reaction of a sterol fatty acid ester at 40° C. for 24 hours while stirring. The reaction solution was washed with hot water, dehydrated at 100° C. and then filtered to remove the enzyme protein.

The resulting product was subjected to molecular distillation using a centrifugal molecular distillation apparatus at a vacuum pressure of 1.5 Pa and an evaporating surface temperature of 230° C. to remove unreacted fatty acids and sterols as a distillate. The residue was subjected to steam distillation using a batch-type steam distillation apparatus under conditions of a vacuum pressure of 1 kPa, a distillation temperature of 250° C. and a distillation time of 2 hours, thereby giving a sterol fatty acid ester (41 g). The sterol fatty acid ester had weak bitter taste, burnt odor and dark yellow color. It had a melting point of 30.5° C., a trans fatty acid content in the constitutive fatty acids of 7.5 wt %, and a sterol fatty acid ester content of 58.9 wt %. The analytic results are shown in Table 3.

COMPARATIVE EXAMPLE 5

The vegetable oil deodorizer distillate was subjected to hydrolysis of fatty acid esters, molecular distillation and synthesis reaction of a sterol fatty acid ester in the same manner as in Example 5. The resulting product was dehydrated and then subjected to molecular distillation using a centrifugal molecular distillation apparatus at a vacuum pressure of 1.5 Pa and an evaporating surface temperature of 230° C. to remove unreacted fatty acids and sterols as a distillate. The residue was subjected to steam distillation using a batch-type steam distillation apparatus under conditions of a vacuum pressure of 500 Pa, a distillation temperature of 150° C. and a distillation time of 1 hour. The resulting product was added with activated clay in an amount of 10 wt % based on the weight of the product, stirred at 80° C. for 30 min. under reduced pressure, and then filtered, thereby giving a sterol fatty acid ester (35 g).

The sterol fatty acid ester was pale yellow in color, but had bitter taste and fetid odor. It had a melting point of 30.6° C., a trans fatty acid content in the constitutive fatty acids of 1.7 wt % and a sterol fatty acid ester content of 95.2 wt %. The analytic results are shown in Table 3.

TABLE 2

| | | Ex. 5 | Ex. 6 | Ex. 7 | Ex. 8 | Ex. 9 | Ex. 10 |
|---|---|---|---|---|---|---|---|
| Sterol fatty acid ester content | TLC-FID % | 95.8 | 95.2 | 96.1 | 95.9 | 96.1 | 94.7 |
| Peroxide value (POV) | meg/kg | 1.5 | 2.1 | 1.2 | 1.9 | 1.8 | 2.3 |
| Acid value (AV) | mg-KOH/g | 0.2 | 0.3 | 0.2 | 0.2 | 0.3 | 0.3 |
| Color | Gardner scale | 4 | 2 | 4 | 4 | 4 | 5 |
| Odor | Sensory test | almost odorless | almost odorless | almost odorless | almost odorless | almost odorless | almost odorless |
| Taste | Sensory test | tasteless | tasteless | tasteless | tasteless | tasteless | tasteless |
| Trans fatty acid content | GC area % | 1.2 | 1.3 | 1.0 | 0.4 | 0.2 | 1.8 |
| Melting point | ° C. | 30.1 | 31.5 | 31.2 | 34.7 | 68.5 | 15.1 |

TABLE 3

| | | C. Ex. 3 | C. Ex. 4 | C. Ex. 5 |
|---|---|---|---|---|
| Sterol fatty acid ester content | TLC-FID % | 59.2 | 58.9 | 95.2 |
| Peroxide value (POV) | meq/kg | 15.6 | 3.6 | 4.3 |
| Acid value (AV) | mg-KOH/g | 2.6 | 0.8 | 0.5 |
| Color | Gardner scale | 16 | 12 | 5 |

TABLE 3-continued

|  |  | C. Ex. 3 | C. Ex. 4 | C. Ex. 5 |
|---|---|---|---|---|
| Odor | Sensory test | strong fetid odor | fetid odor | fetid odor |
| Taste | Sensory test | very strong bitter taste | weak bitter taste | weak bitter taste |
| Trans fatty acid content | GC area % | 4.8 | 7.5 | 1.7 |
| Melting point | °C. | 29.8 | 30.8 | 30.6 |

(C) Examples of the third aspect of the present invention will be described hereinbelow.

EXAMPLE 11

Soybean oil deodorizer distillate (sterol content: 12.3 wt %) (100 g) was added with a 0.2N solution of potassium hydroxide (KOH) in ethanol (5 ml), and stirred at 60° C. for 2 hours to hydrolyze fatty acid esters including triacylglycerol. The reaction solution was neutralized with 0.4N hydrochloric acid, washed with water to remove ethanol, KCl, KOH and glycerin, and then dehydrated at 80° C. under reduced pressure. The resulting product was added with a suspension of lipolytic enzyme powder capable of selectively acting on cis fatty acids originated from a microorganism of the genus Candida (360,000 units/g: "Lipase OF", a product by Meito Sangyo Co., Ltd.) (0.15 g) in water (25 ml). The resulting mixture was subjected to a synthetic reaction of a sterol fatty acid ester at 40° C. for 24 hours while stirring. The reaction solution was heated to 80° C. and stirred at that temperature for 30 min. to inactivate the enzyme. The reaction product was washed with hot water, dehydrated at 80° C. under reduced pressure, added with diatom earth (1.0 g), stirred, and then filtered to remove the enzyme protein.

As the first purification step, the resulting product was subjected to molecular distillation using a centrifugal molecular distillation apparatus at a vacuum pressure of 1.5 Pa and an evaporating surface pressure of 230° C. to remove unreacted fatty acids and sterols as a distillate. As the second purification step, the residue was added with a mixture of activated clay and silica gel (1:1 by weight) in an amount of 10 wt % based on the weight of the residue. The mixture was stirred at 80° C. for 30 min. under reduced pressure and then filtered to remove the activated clay having coloring components adsorbed thereon. Finally, as the third purification step, the resulting product was subjected to steam distillation using a batch-type steam distillation apparatus under conditions of a vacuum pressure of 500 Pa, a distillation temperature of 150° C. and a distillation time of 1 hour, thereby giving a sterol fatty acid ester without odorous components (19 g) as the end product.

The sterol fatty acid ester was almost tasteless, odorless and pale yellow in color, and had a trans fatty acid content in the constitutive fatty acids of 1.4 wt %. The analytic results are shown in Table 4.

EXAMPLE 12

Soybean oil deodorizer distillate (sterol content: 12.3 wt %) (100 g) was treated in the same manner as in Example 11 to hydrolyze the fatty acids therein. The resultant product was dehydrated, and added with a suspension of lipolytic enzyme powder capable of selectively acting on cis fatty acids originated from a microorganism of the genus Mucor (80,000 units/g) (0.7 g) in water (25 ml). The resulting mixture was subjected to a synthetic reaction of a sterol fatty acid ester at 40° C. for 24 hours while stirring. The reaction solution was heated to 80° C. and stirred at that temperature for 30 min. to inactivate the enzyme. The reaction product was washed with hot water, dehydrated at 80° C. under reduced pressure, added with diatom earth (1.0 g), stirred, and then filtered to remove the enzyme protein.

The resulting product was subjected to molecular distillation (i.e., first purification step), treatment with an adsorbent (i.e., second purification step) and steam distillation (i.e., third purification step) in the same manner as in Example 11, thereby giving a sterol fatty acid ester (17 g).

The sterol fatty acid ester was almost tasteless, odorless and pale yellow in color, and had a trans fatty acid content in the constitutive fatty acids of 1.1 wt %. The analytic results are shown in Table 4.

COMPARATIVE EXAMPLE 6

Soybean oil deodorizer distillate (sterol content: 12.3 wt %) (100 g) was subjected to hydrolysis of fatty acid esters in the same manner as in Example 11 and then dehydrated. The resulting product was added with a suspension of lipolytic enzyme powder having no selective activity originated from a microorganism of the genus Pseudomonas (50,000 units/g: "Lipase TL", a product by Meito Sangyo Co., Ltd.) (1.0 g) in water (25 ml). The resulting mixture was subjected to a synthetic reaction of a sterol fatty acid ester at 40° C. for 24 hours while stirring. The reaction solution was heated to 80° C. and stirred at that temperature for 30 min. to inactivate the enzyme. The reaction product was washed with hot water, dehydrated at 80° C. under reduced pressure, added with diatom earth (1.0 g), stirred, and then filtered to remove the enzyme protein.

The resulting product was subjected to molecular distillation (i.e., first purification step), treatment with an adsorbent (i.e., second purification step) and steam distillation (i.e., third purification step) in the same manner as in Example 11, thereby giving a sterol fatty acid ester (17 g).

The sterol fatty acid ester was almost tasteless, odorless and pale yellow in color, but had a trans fatty acid content in the constitutive fatty acids of 5.5 wt %. The analytic results are shown in Table 4.

TABLE 4

|  |  | Ex. 11 | Ex. 12 | C. Ex. 6 |
|---|---|---|---|---|
| Sterol fatty acid ester content | TLC-FID % | 96.8 | 95.6 | 94.9 |
| Peroxide value (POV) | meq/kg | 1.6 | 2.1 | 1.9 |
| Acid value (AV) | mg-KOH/g | 0.3 | 0.4 | 0.8 |
| Color | Gardner scale | 4 | 4 | 5 |
| Odor | Sensory test | almost odorless | almost odorless | almost odorless |
| Taste | Sensory test | tasteless | tasteless | tasteless |
| Trans fatty acid content | GC area % | 1.4 | 1.1 | 5.5 |

According to the present invention, as described above, a vegetable oil deodorizer distillate derived from a plant oil is used as a starting material, the synthetic reaction of a sterol fatty acid ester is performed using a lipase as a catalyst under strictly controlled conditions, and the synthesized sterol fatty acid ester is purified through several steps of purification process in order to provide qualities suitable for a food material. Accordingly, the present invention has an advantage that an inexpensive dietary sterol fatty acid ester having a potential physiological activity and superior qualities.

Furthermore, according to the present invention, as another aspect, a vegetable oil deodorizer distillate which is produced as a distillate containing volatile components in the deodorization step (a step included in the purification process) of a vegetable oil is used as a starting material. Fatty acid esters, e.g., triacylglycerol, in the vegetable oil deodorizer distillate are previously degraded by hydrolysis with a chemical catalyst, and fatty acids generated in the hydrolysis are then removed by the first molecular distillation to give a sterol-containing fraction. The sterol-containing fraction is added with a fat and oil primarily comprising triacylglycerol. The mixture is used as the starting material and the synthetic reaction of a sterol fatty acid ester is performed using a lipolytic enzyme as a catalyst under strictly controlled conditions. The resulting product undergoes several steps of purification process in order to provide qualities suitable for a food material. In this manner, a highly safe, inexpensive dietary sterol fatty acid ester which contains little deteriorated fatty acids including trans fatty acids can be produced enzymatically.

Still further, according to the present invention, as still another aspect, a vegetable oil deodorizer distillate which is produced as a distillate containing volatile components in the deodorization step (a step included in the purification process) of a vegetable oil is used as a starting material. Fatty acid esters, e.g., triacylglycerol, in the vegetable oil deodorizer distillate are previously degraded by hydrolysis with a chemical catalyst. The resulting product undergoes a synthetic reaction of a sterol fatty acid ester under strictly controlled conditions using a lipolytic enzyme capable of selectively acting on cis fatty acids as a catalyst. The resulting product undergoes several steps of purification process in order to provide qualities suitable for a food material. In this manner, a highly safe, inexpensive dietary sterol fatty acid ester which contains little trans fatty acids can be produced enzymatically.

What is claimed is:

1. A process for enzymatically producing a dietary sterol fatty acid ester using a lipolytic enzyme as a catalyst, the process comprising:

providing a vegetable oil deodorizer distillate as a starting material, and performing a synthetic reaction of a sterol fatty acid ester from the vegetable oil deodorizer distillate using a lipolytic enzyme for a predetermined time period under the conditions where temperature and water content are controlled;

performing inactivation of the enzyme, dehydration and removal of the enzyme protein;

performing a molecular distillation to primarily remove unreacted sterols and fatty acids;

treating the resulting product with an adsorbent to primarily remove coloring components; and then performing a steam distillation to primarily remove odorous components, the sterol fatty acid ester being physiologically active, superior in flavor properties and safety for food.

2. The process for enzymatically producing a sterol fatty acid ester according to claim 1, wherein the vegetable oil deodorizer distillate is from soybean which is produced in the refining process for soybean oil.

3. The process for enzymatically producing a sterol fatty acid ester according to claim 1, wherein the lypolytic enzyme is a lipase or cholesterol esterase.

4. The process for enzymatically producing a sterol fatty acid ester according to claim 1, wherein the lipase is a mesophilic lipase, and the synthetic reaction of a sterol fatty acid ester is performed at 30 to 50° C. within 48 hours.

5. The process for enzymatically producing a sterol fatty acid ester according to claim 1, wherein the lipase is a thermostable lipase, and the synthetic reaction of a sterol fatty acid ester is performed at 50 to 80° C. within 24 hours.

6. The process for enzymatically producing a dietary sterol fatty acid ester according to claim 1, wherein the synthetic reaction of a sterol fatty acid ester is performed using a lipase in the presence of water in an amount of 0.1 wt % or more based on the weight of the starting material.

7. The process for enzymatically producing a sterol fatty acid ester according to claim 1, wherein the molecular distillation is performed using a molecular distillation apparatus at 133 Pa or lower and 100 to 300° C.

8. The process for enzymatically producing a sterol fatty acid ester according to claim 1, wherein the treatment with an adsorbent is performed using, as the adsorbent, activated clay, silica gel, activated carbon or a mixture of two or more of them in an amount of 0.1 to 50 wt % based on the weight of the materials to be treated in the presence of a non-polar solvent.

9. The process for enzymatically producing a sterol fatty acid ester according to claim 1, wherein the steam distillation is performed at 13.3 kPa or lower and 50 to 250° C.

10. The process for enzymatically producing a sterol fatty acid ester according to claim 1, wherein the end product sterol fatty acid ester has a sterol fatty acid ester content of 90 wt % or more, a peroxide value of 15 or lower, an acid value of 3 or lower and a Gardner color scale of 8 or lower and is almost odorless as determined by a sensory test.

11. A method for using a sterol fatty acid ester produced by a process as recited in claim 1 for food in the form where the sterol fatty acid ester is previously mixed with a fat and oil primarily comprising triacylglycerol.

12. A process for producing a dietary sterol fatty acid ester comprising adding a lipolytic enzyme to a mixture of a sterol-containing fraction and a fat and oil primarily comprising triacylglycerol to produce a sterol fatty acid ester and then purifying the sterol fatty acid ester through a predetermined purification process, the process comprising:

providing, as a source of sterols, a vegetable oil deodorizer distillate which is produced in the deodorization process of a vegetable oil;

performing hydrolysis of fatty acid esters in the vegetable oil deodorizer distillate;

performing a first molecular distillation to primarily remove fatty acids to collect a sterol-containing fraction;

performing a synthetic reaction of a sterol fatty acid ester using a mixture of the sterol-containing fraction and a fat and oil primarily comprising triacylglycerol as a starting material, with a lipolytic enzyme for a predetermined time period under the conditions where temperature and water content are controlled;

as a first purification step, performing a second molecular distillation to primarily remove unreacted sterols and fatty acids;

as a second purification step, treating the resulting product with an adsorbent to primarily remove coloring components; and then as a third purification step, performing steam distillation to primarily remove odorous components, while controlling the temperature for the purification to prevent the production of trans fatty acids, the sterol fatty acid ester being superior in physical properties, flavor properties and safety for food.

13. The process for enzymatically producing a sterol fatty acid ester according to claim 12, wherein the hydrolysis is performed for the purpose of removing easily trans fatty acids and deteriorated fatty acids such as oxidized fatty acids as their free states from the vegetable oil deodorizer distillate.

14. The process for enzymatically producing a sterol fatty acid ester according to claim 12, wherein soybean oil deodorizer distillate which is produced in the refining process of soybean oil is used as the source of sterols.

15. The process for enzymatically producing a sterol fatty acid ester according to claim 12, wherein the hydrolysis is performed using an acidic or alkaline catalyst.

16. The process for enzymatically producing a sterol fatty acid ester according to claim 12, wherein the first molecular distillation is performed at 13.3 Pa or lower and 100 to 200° C.

17. The process for enzymatically producing a sterol fatty acid ester according to claim 12, wherein, in the first molecular distillation, the reaction mixture is distilled at 13.3 Pa or lower and 100 to 200° C. to collect a sterol-containing fraction as a residue and the sterol-containing fraction is then distilled at 13.3 Pa or lower and 170 to 250° C. to collect a sterol-containing fraction as a distillate.

18. The process for enzymatically producing a sterol fatty acid ester according to claim 12, wherein the synthetic reaction of a sterol fatty acid ester is performed using a lipolytic enzyme having an activity of hydrolyzing a sterol fatty acid ester as the lipolytic enzyme.

19. The process for enzymatically producing a sterol fatty acid ester according to claim 12, wherein the synthetic reaction of a sterol fatty acid ester is performed using an enzyme capable of hydrolyzing a sterol fatty acid ester which is originated from a microorganism of the genus Pseudomonas as the lipolytic enzyme.

20. The process for enzymatically producing a sterol fatty acid ester according to claim 12, wherein the lipolytic enzyme is a cholesterol esterase.

21. The process for enzymatically producing a sterol fatty acid ester according to claim 12, wherein the synthetic reaction of a sterol fatty acid ester is performed using an enzyme having an activity of hydrolyzing triacylglycerol as the lipolytic enzyme.

22. The process for enzymatically producing a sterol fatty acid ester according to claim 12, wherein the synthetic reaction of a sterol fatty acid ester is performed using an enzyme capable of hydrolyzing triacylglycerol which is originated from a microorganism of the genus Candida as the lipolytic enzyme.

23. The process for enzymatically producing a sterol fatty acid ester according to claim 21 or 22, wherein the lipolytic enzyme is a lipase.

24. The process for enzymatically producing a sterol fatty acid ester according to claim 12, wherein the synthetic reaction of a sterol fatty acid ester is performed at 30 to 60° C. within 48 hours in the presence of water of 0.1 to 50 wt % based on the weight of the fat and oil primarily comprising triacylglycerol.

25. The process for enzymatically producing a sterol fatty acid ester according to claim 12, wherein the second molecular distillation as the first purification step is performed at 13.3 Pa or lower and 100 to 250° C.

26. The process for enzymatically producing a sterol fatty acid ester according to claim 12, wherein the treatment with an adsorbent as the second purification step is performed at 100° C. or lower using, as the adsorbent, activated clay, silica gel, activated carbon or a mixture of two or more of them in an amount of 0.1 to 50 wt % based on the weight of the material to be treated.

27. The process for enzymatically producing a sterol fatty acid ester according to claim 12, wherein the steam distillation as the third purification step is performed at 1330 Pa or lower and 50 to 150° C.

28. The process for enzymatically producing a sterol fatty acid ester according to claim 12, wherein the end product sterol fatty acid ester has a sterol fatty acid ester content of 90 wt % or more, a trans fatty acid content in the constitutive fatty acids of 2 wt % or lower, a peroxide value of 10 or lower, an acid value of 1 or lower and a Gardner color scale of 6 or lower and is almost odorless as determined by a sensory test.

29. The process for enzymatically producing a sterol fatty acid ester according to claim 12, wherein soybean oil is used as the fat and oil primarily comprising triacylglycerol to be added to the sterol-containing fraction, and the end product sterol fatty acid ester has a melting point of 20 to 40° C. and a trans fatty acid content in the constitutive fatty acids of 2 wt % or lower.

30. The process for enzymatically producing a sterol fatty acid ester according to claim 12, wherein rapeseed oil is used as the fat and oil primarily comprising triacylglycerol to be added to the sterol-containing fraction, and the end product sterol fatty acid ester has a melting point of 20 to 40° C. and a trans fatty acid content in the constitutive fatty acids of 2 wt % or lower.

31. The process for enzymatically producing a sterol fatty acid ester according to claim 12, wherein olive oil is used as the fat and oil primarily comprising triacylglycerol to be added to the sterol-containing fraction, and the end product sterol fatty acid ester has a melting point of 25 to 45° C. and a trans fatty acid content in the constitutive fatty acids of 1 wt % or lower.

32. The process for enzymatically producing a sterol fatty acid ester according to claim 12, wherein palm oil is used as the fat and oil primarily comprising triacylglycerol to be added to the sterol-containing fraction, and the end product sterol fatty acid ester has a melting point of 40 to 100° C. and a trans fatty acid content in the constitutive fatty acids of 1 wt % or lower.

33. The process for enzymatically producing a sterol fatty acid ester according to claim 12, wherein palm oil is used as the fat and oil primarily comprising triacylglycerol to be added to the sterol-containing fraction, a thermostable lipolytic enzyme is used, and the end product sterol fatty acid ester has a melting point of 40 to 100° C. and a trans fatty acid content in the constitutive fatty acids of 1 wt % or lower.

34. The process for enzymatically producing a sterol fatty acid ester according to claim 12, wherein a fish oil is used as the fat and oil primarily comprising triacylglycerol to be added to the sterol-containing fraction, and the end product sterol fatty acid ester has a melting point of −10 to 20° C. and a trans fatty acid content in the constitutive fatty acids of 2 wt % or lower.

35. A process for enzymatically producing a dietary sterol fatty acid ester comprising adding a lipolytic enzyme to a mixture of a starting material containing sterols and a fat and oil primarily comprising triacylglycerol to produce a sterol fatty acid ester and then purifying the sterol fatty acid ester in a predetermined purification process, the process comprising:

providing, as a starting material, a vegetable oil deodorizer distillate which is produced in the deodorization process of a vegetable oil;

performing hydrolysis of fatty acid esters in the vegetable oil deodorizer distillate;

performing a synthetic reaction of a sterol fatty acid ester from the mixture with a lipolytic enzyme capable of selectively acting on cis fatty acids for a predetermined time period under the conditions where temperature and water content are controlled;

as a first purification step, performing molecular distillation to primarily remove unreacted sterols and fatty acids;

as a second purification step, treating the resulting product with an adsorbent to primarily remove coloring components; and then as a third purification step, performing steam distillation to primarily remove odorous components, the sterol fatty acid ester being superior in flavor properties and safety.

36. The process for enzymatically producing a sterol fatty acid ester according to claim 35, wherein soybean oil deodorizer distillate which is produced in the refining process of soybean oil is used as the starting material.

37. The process for enzymatically producing a sterol fatty acid ester according to claim 35, wherein the hydrolysis is performed using an acidic or alkaline catalyst.

38. The process for enzymatically producing a sterol fatty acid ester according to claim 35, wherein the synthetic reaction of a sterol fatty acid ester is performed using a lipolytic enzyme capable of selectively acting on cis fatty acids which is originated from a microorganism of the genus Candida or Mucor.

39. The process for enzymatically producing a sterol fatty acid ester according to claim 35, wherein the synthetic reaction of a sterol fatty acid ester is performed at 30 to 60° C. within 48 hours in the presence of water of 0.1 to 50 wt % based on the weight of the starting material.

40. The process for enzymatically producing a sterol fatty acid ester according to claim 35, wherein the molecular distillation as the first purification step is performed at 13.3 Pa or lower and 100 to 250° C.

41. The process for enzymatically producing a sterol fatty acid ester according to claim 35, wherein the treatment with an adsorbent as the second purification step is performed at 100° C. or lower using, as the adsorbent, activated clay, silica gel, activated carbon or a mixture of two or more of them in an amount of 0.1 to 50 wt % based on the weight of the material to be treated.

42. The process for enzymatically producing a sterol fatty acid ester according to claim 35, wherein the steam distillation as the third purification step is performed at 1330 Pa or lower and 50 to 150° C.

43. The process for enzymatically producing a sterol fatty acid ester according to claim 35, wherein the end product sterol fatty acid ester has a sterol fatty acid ester content of 90 wt % or more, a trans fatty acid content in the constitutive fatty acids of 2 wt % or lower, a peroxide value of 10 or lower, an acid value of 1 or lower and a Gardner color scale of 6 or lower and is almost odorless as determined by a sensory test.

* * * * *